(12) United States Patent
Agarwal

(10) Patent No.: US 12,340,872 B2
(45) Date of Patent: Jun. 24, 2025

(54) SYSTEMS AND METHODS FOR ENGINEERING ENZYMES USING IDENTIFIED ENERGY TRANSFER NETWORKS

(71) Applicant: Arium BioLabs LLC, Knoxville, TN (US)

(72) Inventor: Pratul K. Agarwal, Knoxville, TN (US)

(73) Assignee: Arium BioLabs LLC, Edmond, OK (US)

( * ) Notice: Subject to any disclaimer, the term of this patent is extended or adjusted under 35 U.S.C. 154(b) by 882 days.

(21) Appl. No.: 17/068,371

(22) Filed: Oct. 12, 2020

(65) Prior Publication Data

US 2021/0110884 A1  Apr. 15, 2021

Related U.S. Application Data

(60) Provisional application No. 62/914,151, filed on Oct. 11, 2019.

(51) Int. Cl.

| | |
|---|---|
| *G16B 15/00* | (2019.01) |
| *C12N 9/06* | (2006.01) |
| *C12N 9/18* | (2006.01) |
| *C12N 9/90* | (2006.01) |
| *G16B 5/00* | (2019.01) |

(52) U.S. Cl.
CPC ............ *G16B 15/00* (2019.02); *C12N 9/003* (2013.01); *C12N 9/18* (2013.01); *C12N 9/90* (2013.01); *C12Y 105/01003* (2013.01); *C12Y 301/01008* (2013.01); *C12Y 502/01008* (2013.01); *G16B 5/00* (2019.02)

(58) Field of Classification Search
CPC .......... G16B 15/00; G16B 5/00; G16B 15/20; G16B 15/30; G16B 20/00; C12N 9/003; C12N 9/18; C12N 9/90; C12Y 105/01003; C12Y 301/01008; C12Y 502/01008

See application file for complete search history.

(56) References Cited

U.S. PATENT DOCUMENTS

| | | | |
|---|---|---|---|
| 6,553,317 B1 * | 4/2003 | Lincoln ............... | G16B 50/30 435/6.12 |
| 8,417,461 B2 | 4/2013 | Agarwal | |
| 9,195,795 B2 | 11/2015 | Agarwal | |
| 11,621,053 B2 | 3/2023 | Agarwal | |
| 2003/0087306 A1 | 5/2003 | Christensen et al. | |
| 2017/0356024 A1 | 12/2017 | Kern | |

FOREIGN PATENT DOCUMENTS

| | | | | |
|---|---|---|---|---|
| WO | WO-2009098596 A2 * | 8/2009 | ............ | G01N 33/68 |
| WO | 2013003358 A2 | 1/2013 | | |

OTHER PUBLICATIONS

Petrounia IP and Arnold FH. Designed evolution of enzymatic properties. Current Opinion in Biotechnology 11(4): 325-330. (Year: 2000).*
Bernal C. Integrating enzyme immobilization and protein engineering: an alternative path for the development of novel and improved industrial biocatalysts. Biotechnology Advances 36(5): 1470-1480. (Year: 2018).*
Bartlett GJ. Analysis of catalytic residues in enzyme active sites. Journal of Molecular Biology 324: 105-121. (Year: 2002).*
Zhang X-F. A general and efficient strategy for generating the stable enzymes. Scientific Reports 6: 33797, 10 pages. (Year: 2016).*
Agarwal, A Biophysical Perspective on enzyme Catalysis, Biochemistry 2019, vol. 58, pp. 438-449.
Agarwal, Role of Protein Dynamics in Reaction Rate Enhancement by Enzymes, Journal of American Chemical Society, vol. 127, pp. 15248-15256 (2005).
Ramanathan, et al. Evolutionarily Conserved Linkage Between Enzyme Fold, Flexibility, and Catalysis, PLOS Biology, vol. 9, Issue 11, pp. 1-18 (Nov. 2011).
Chennubhotla, et al., Signal Propagation in Proteins and Relation to Equilibrium Fluctuations, PLOS Computational Biology, vol. 3, Issue 9, pp. 1716-1727 (Sep. 2007).
McClendon, et al., Quantifying Correlations Between Allosteric Sites in Thermodynamic Ensembles, Journal of Chemical Theory and Computation, vol. 5, No. 9, pp. 2486-2502 (2009).
Ramanathan, et al. Computational Identification of Slow Conformational Fluctuations in Proteins, J. Phys. Chem. B., vol. 113, pp. 16669-16680 (2009).
Yu et al., Heat Flow in Proteins: Computation of Thermal Transport Coefficients, The Journal of Chemical Physics, vol. 122, pp. 54902-1-054902-11 (2005).
Xie et al., Excited-State Lifetimes of Far-Infrared Collective Modes in Proteins, The American Physical Society, Physical Review Letters, vol. 88, pp. 018102-1-018102-4 (Jan. 7, 2002).

(Continued)

*Primary Examiner* — Olivia M. Wise
*Assistant Examiner* — Robert J. Kallal
(74) *Attorney, Agent, or Firm* — MERCHANT & GOULD P.C.

(57) ABSTRACT

The present disclosure is directed to methods and systems for identifying different parts of enzyme structure that can be engineered and/or assisted by engineered technologies to improve the speed and efficiency of the catalyzed chemical reactions. More specifically, the present disclosure is directed to identifying and modifying distal surface regions that affect catalytic activity. These surface regions are identified and ranked for the impact on enzyme activity, based on the transfer of energy from the surface regions to the active site. Methods are described for improving the catalytic efficiency by improving the energy transfer to overcome the activation energy barrier. The methods described are also applicable for improving the stability of enzymes and development of appropriate enzyme immobilization protocols.

27 Claims, 23 Drawing Sheets

(19 of 23 Drawing Sheet(s) Filed in Color)

(56) References Cited

OTHER PUBLICATIONS

Ramanathan et al., Protein Conformational Populations and Functionally Relevant Substates, Accounts of Chemical Research, vol. 47, No. 1, pp. 149-156 (2013).
Ramanathan et al., Discovering Conformational Sub-States Relevant to Protein Function, PLOS One, vol. 6, Issue 1, pp. 1-16 (Jan. 2011).
Boehr et al., The Dynamic Energy Landscape of Dihydrofolate Reductase Catalysis, Science, vol. 313, pp. 1638-1642 (Sep. 15, 2006).
Ichiye et al., Anisotropy and Anharmonicity of Atomic Fluctuations in Proteins: Implications for X-ray Analysis, Biochemistry, vol. 27, No. 9, pp. 3487-3497 (1988).
Kenakin, Allosteric Modulators: The New Generation of Receptor Antagonist, Molecular Interventions, vol. 4, Issue 4, pp. 222-229 (Aug. 2004).
Zhang et al., Targeting Bcr-Abl by Combining Allosteric with ATP-Binding-Site Inhibitors, Nature, vol. 463, pp. 501-507 (Jan. 28, 2010).
Lopez-Garcia et al., Allosteric Regulation of Protein Kinase PKC by the N-Terminal C1 Domain and Small Compounds to the PIF-Pocket, Chemistry & Biology, vol. 18, pp. 1463-1473 (Nov. 23, 2011).
Christopoulos, Allosteric Binding Sites on Cell-Surface Receptors: Novel Targets for Drug Discovery, Nature Reviews Drug Discovery, vol. 1, pp. 198-210 (Mar. 2002).
Kar et al., Allostery and Population Shift in Drug Discovery, Current Opinion in Pharmacology, vol. 10, pp. 715-722 (2010).
Eathiraj et al., Discovery of a Novel Mode of Protein Kinase Inhibition Characterized by the Mechanism of Inhibition of Human Mesenchymal-Epithelial Transition Factor (c-Met) Protein Autophosphorylation by ARQ 197, Journal of Biological Chemistry, vol. 286, No. 23, pp. 20666-20676 (Jun. 10, 2011).
Dettori et al., Regulation of the Interaction Between Protein Kinase C-Related Protein Kinase 2 (PRK2) and Its Upstream Kinase, 3-Phosphoinositide-Dependent Protein Kinase 1 (PDK1), Journal of Biological Chemistry, vol. 284, No. 44, pp. 30318-30327 (Oct. 30, 2009).
Hindie et al., Structure and Allosteric Effects of Low-Molecular-Weight Activators on the Protein Kinase PDK1, Nature Chemical Biology, vol. 5, No. 10, pp. 758-764 (Oct. 2009).
Perryman, Alexander L. et al., Virtual screening with Autodock Vina and the common pharmacophore engine of a low diversity library of fragment and hit against the three allosteric sites of HIV integrase: participation in the SAMPL4 protein-ligand binding challenge; J Comput Aided Mol Des (2014) 28:429-441; DOI 10.1007/s10822-014-9709-3.
Narayanan, Chitra et al., Applications of NMR and computational methodologies to study protein dynamics, Review article in Archives of Biochemistry and Biophysics 628 (2017) pp. 71-80.
Lu, Shaoyong et al. Allosteric modulator Discovery: From Serendipity to Structure-Based Design; Journal of Medicinal Chemistry, J. Med. Chem. 2019, 62, 6405-6421.
Huang, Wenkang et al., Computational tools for Allosteric Drug Discovery: Site Identification and Focus Library Design, HHS Public Access Author manuscript, Methods Mol Biol. 2017; 1529: 439-446. doi: 10.1007/978-1-4939-6637-0_23.

\* cited by examiner

SYSTEMS AND METHODS FOR ENGINEERING ENZYMES USING IDENTIFIED ENERGY TRANSFER NETWORKS

BACKGROUND

Enzymes are naturally occurring biological catalysts. They are commonly utilized in industrial applications, food products, animal feed, food preparation, house-hold products, medicinal therapies and in a variety of laboratory scale processes. Naturally occurring enzymes and their modified versions are used to improve the speed of reactions which are too slow to occur on their own or would not occur at all.

In many applications engineered versions of enzymes are highly desired, as the naturally occurring enzymes do not provide the required speed for the reaction and/or they do not withstand the operating conditions. For example, in industrial applications it is highly desirable to have enzymes that are able to tolerate high temperatures and other harsh conditions including acidic or alkaline environments. Technologies that provide increased enzyme stability during storage and maintain enzyme viability over extended periods of time are also highly desired. Additionally, more efficient enzymes which enable a desired reaction to proceed at a much faster rate allow for time and cost savings. Therefore, engineering of enzymes has been widely pursued for developing better suited and more efficient versions in various applications. In particular, technologies which improve the stability of enzymes and their catalytic efficiencies are the most sought after.

A number of approaches and techniques are available for engineering of enzymes, but achieving desired improvements in the efficiency and stability enzymes is not always possible. This is an indication of a fundamental lack of understanding of factors that control efficiency and other aspects of enzyme catalysis. A new approach which is based on addressing this issue will have a wide impact through development of more efficient enzymes as well as enzymes that are able to tolerate a wide range of operating conditions.

SUMMARY

This disclosure is directed at engineering enzymes that improve the speed and efficiency of catalyzed reactions and provide optimal enzymes in desired conditions. This disclosure further provides methods and systems for manipulating regions of enzymes and also enables designing of related small compounds or large molecules that enable enzymes to achieve better efficiency and more stability.

In particular, the invention is based on the new understanding of protein structure, dynamics and function with the role of surrounding environment in protein activity. Further understanding of conformational fluctuations that enable the activity of the protein target allows identification of functionally critical conformational sub-states. This, in turn, allows for discovery of distal regions of enzyme's structure that are optimized for improving the thermodynamical coupling between the enzyme surface and the surrounding environment. This disclosure provides methods for identifying functionally important surface regions of enzymes and approaches to optimize the energy flow between these regions and the surrounding solvent and the environment. Using the fundamental knowledge of factors that enable enzymes to achieve their catalytic efficiency, new versions of more efficient and more stable enzymes can be developed.

In one aspect, a method of engineering a target enzyme to modify its catalytic activity comprises: accessing biophysical and dynamics data for the target enzyme; analyzing, using a computing device, the biophysical and dynamics data to identify at least one energy transfer network within the target enzyme, the at least one energy transfer network comprising a series of residues spanning from a surface of the target enzyme to a catalytic site of the target enzyme; identifying at least one surface loop within the energy transfer network, the at least one surface loop comprising a plurality of residues showing dynamical motions coupled to the catalytic activity of the target enzyme; and modifying one or more of the plurality of residues in the at least one surface loop to produce an engineered enzyme sequence.

In another aspect, a system for engineering enzymes comprises: a processing device; an enzyme database; and a memory device in communication with the processing device. The memory device comprises instructions that, when executed by the processing device, cause the system to: receive input at a user interface selecting a target enzyme; access biophysical and dynamics data for the target enzyme from the enzyme database; analyze the biophysical and dynamics data to identify an energy transfer network within the target enzyme, the energy transfer network comprising a series of residues spanning from a surface of the target enzyme to a catalytic site of the target enzyme; identify a surface loop within the energy transfer network, the surface loop comprising a plurality of residues showing dynamical motions coupled to the catalytic activity of the target enzyme; analyze a secondary structure of the target enzyme to identify one or more locations within the surface loop to modify; modify one or more residues in at least one of the one or more locations in the surface loop to produce an engineered enzyme; and output an amino acid sequence of the engineered enzyme on the user interface.

In yet another aspect, one or more non-transitory computer-readable media have computer-executable instructions embodied thereon that, when executed by one or more computing devices, cause the computing devices to: receive input at a user interface selecting a target enzyme; access biophysical and dynamics data for the target enzyme from the enzyme database; analyze the biophysical and dynamics data to identify at least one energy transfer network within the target enzyme, the at least one energy transfer network comprising a series of residues spanning from a surface of the target enzyme to a catalytic site of the target enzyme; identify at least one surface loop within the energy transfer network, the at least one surface loop comprising a plurality of residues showing dynamical motions coupled to the catalytic activity of the target enzyme; analyze a secondary structure of the target enzyme to identify one or more locations within the at least one surface loop to modify; modify at least one of the plurality of residues in at least one of the one or more locations in the at least one surface loop to produce an engineered enzyme; model the engineered enzyme in complex with a substrate using molecular dynamics simulations; analyze substrate kinetics of the engineered enzyme and the substrate; output an amino acid sequence of the engineered enzyme on the user interface; and store the amino acid sequence of the engineered enzyme in an engineered enzyme data store.

In another aspect, a method of engineering a target enzyme to enhance its catalytic activity includes: accessing biophysical and dynamics data for the target enzyme; analyzing, using a computing device, the biophysical and dynamics data to identify at least one energy transfer network within the target enzyme, the at least one energy transfer network comprising a series of residues spanning from a surface of the target enzyme to a catalytic site of the target enzyme; identifying at least one surface loop within the energy transfer network, the at least one surface loop comprising a plurality of residues showing dynamical motions coupled to the catalytic activity of the target enzyme; analyzing a secondary structure of the target enzyme to identify one or more locations within the surface loop to modify; modifying one or more of the plurality of residues in the surface loop to produce an enhanced enzyme sequence; modeling the engineered enzyme in complex with a substrate using molecular dynamics simulations; analyzing substrate kinetics of the engineered enzyme; and outputting an amino acid sequence for the enhanced enzyme.

In another aspect, a system for enhancing enzymes includes: a processing device; an enzyme database; and a memory device in communication with the processing device. The memory device includes instructions that, when executed by the processing device, cause the system to: receive input at a user interface displayed on a computing device, the input selecting a target enzyme from the enzyme database; access biophysical and dynamics data for the target enzyme from the enzyme database; analyze the biophysical and dynamics data to identify an energy transfer network within the target enzyme, the energy transfer network comprising a series of residues spanning from a surface of the target enzyme to an active site of the target enzyme; identify at least one surface loop within the energy transfer network, the surface loop comprising a plurality of residues showing dynamical motions coupled to catalytic activity of the target enzyme; analyze a secondary structure of the target enzyme to identify one or more locations within the at least one surface loop to modify; insert at least one additional residue into the plurality of residues in at least one of the one or more locations in the at least one surface loop to produce an enhanced enzyme; and output an amino acid sequence of the enhanced enzyme on the user interface.

In another aspect, a method of identifying small compounds to improve the activity of an enzyme having an industrial application includes: accessing biophysical and dynamics data for the enzyme; analyzing the biophysical and dynamics data to identify one or more potential ligand binding sites located remote from a site of designated activity on the target molecule, the binding sites being energetically coupled to an active site of the enzyme through an energy transfer network; quantifying a level of energetic coupling between each of the one or more potential functionally important binding sites and the active site of the target molecule; ranking each of the identified sites based on suitability as a ligand binding site and quantity of energetic coupling; selecting one or more of the identified sites having the best ranking to produce a subset of identified ligand binding sites; computationally screening a plurality of chemical compounds to determine a binding energy between each of the subset of identified sites and each of the plurality of chemical compounds; computationally modeling a derived set of chemical compounds based on strong binding compounds with different functional groups to improve the binding on the identified sites; computationally modeling the effect of the chemical compounds binding to each of the plurality of identified sites; quantifying each of a plurality of conformations of the enzyme while bound to the chemical compounds and while not bound to the compounds; ranking the chemical compounds based on achieving a conformation of the enzyme that enhances catalytic activity needed for the industrial application; and selecting a subset of top ranking chemical compounds comprising of increasing the activity of the enzyme.

In yet another aspect, a method of engineering a target enzyme to modify its catalytic activity comprises: accessing biophysical and dynamics data for the target enzyme; analyzing, using a computing device, the biophysical and dynamics data to identify at least one energy transfer network within the target enzyme, the at least one energy transfer network comprising a series of residues spanning from a surface of the target enzyme to a catalytic site of the target enzyme; identifying one or more residues within the energy transfer network that are not on the surface of the target enzyme; and modifying the one or more residues to produce an engineered enzyme sequence that has improved energy flow to the catalytic site as compared to the unmodified target enzyme.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
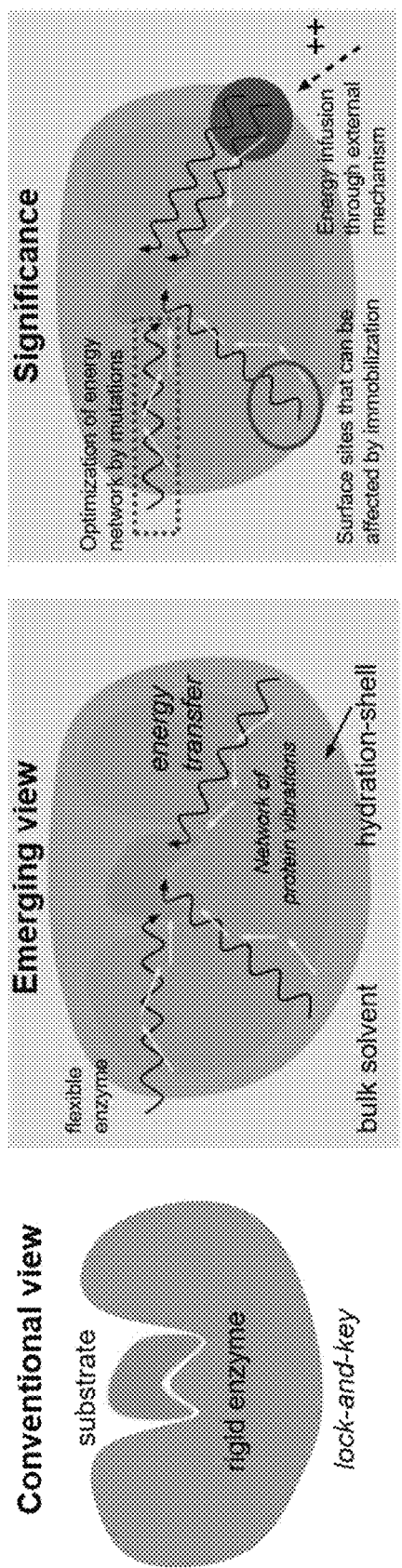
FIG. 1 depicts three schematic representations of an enzyme bound to a substrate, summarizing a current understanding of how enzymes function and their significance for developing more efficient and stable versions of enzymes.

The present disclosure is directed to methods and systems for identifying different parts of enzyme structures that can be engineered and/or assisted by engineered technologies to improve the speed and efficiency of the catalyzed chemical reactions. More specifically, the present disclosure is directed to identifying and modifying distal surface regions that affect catalytic activity.

The present technologies for engineering of enzymes to improve efficiency include mutations particularly in the active site and some version of the directed evolution technique. In the traditional approach of rational enzyme design, significant emphasis is on the structural interactions between the substrate and the enzyme, and therefore the enzyme mechanism is investigated to identify reaction intermediates, and these intermediates are characterized to understand the role of key residues in the active site. The identified residues are then mutated to improve their contribution to the catalyzed reaction through stabilization of the intermediates, thereby aiming to improve the catalytic efficiency. Recently, the technique of directed evolution has led to some limited successes in bio-catalyst engineering. In directed evolution, a large variety of random mutations are created through various molecular biology techniques and the resulting enzymes are screened for beneficial activity. The process is repeated for a number of steps (generations) to reach the desired enzyme efficiency or till no further increase is observed. Directed evolution provides little to no understanding of why mutations achieve better catalysis; therefore, its use is limited as a planned approach to catalyst design. Both these approaches are costly and resource intensive, and the catalytic efficiency of enzymes developed using these approaches still fall $10^5$-$10^6$ fold short of naturally occurring enzymes.

New technologies are widely desired that allow optimization of bio-catalytic processes mediated by enzymes, through designing more efficient enzymes. Recently, there has been push on enzyme engineering through rational design of enzymes, focusing on the entire structure instead of just the active sites. A number of theories have been proposed to explain the high catalytic efficiency or the reaction rate-enhancement achieved by the enzymes. For more than a century, biochemists have known the importance of enzyme structure; the lock-and-key, induced-fit and the transition state stabilization theories have suggested that enzyme function depends on direct structural interaction between the enzyme and the substrate. Investigations based on current approaches provide only incremental changes in understanding; and the insights obtained for individual enzymes typically do not translate into understanding of other systems. This has led to the current paradigm where each enzyme requires its own investigations and its own description of mechanism. More importantly, even after a century of investigations, important and fundamental issues still remain unresolved: (1) How do enzymes accelerate the reactions? What factors are crucial for enzyme catalytic efficiency? (2) What role do the regions outside the active site play in the enzyme mechanisms? (3) Why are residues located >20 Å way from the active site conserved? What role do these distal residues play in enzyme mechanisms? Why does enzyme activity decrease when these residues are mutated? (4) What role does the surrounding environment play, particularly the solvent in the case of soluble proteins?

Here we describe technology that can improve enzyme activity by either (1) improve naturally occurring proteins or other types of natural occurring biomolecules which catalyze chemical or biochemical processes or (2) product synthetic or artificially prepared biomolecules which can serve as enzymes or biological catalysts. In addition, the invented technology also improves operating conditions such that the enzyme can be used in a wide variety of conditions such as the case of immobilized enzymes.

Immobilization is a technique in which the natural or artificially prepared enzyme is attached to a substrate or surface such that it can be reused. Unfortunately, immobilized enzymes can experience decreases in efficiency when compared to their free counterparts. The exact reasons for these decreases of such efficiency are still under debate. The invented technology allows preparing of enzyme molecules and selection of immobilization chemistry such that the immobilized enzymes do not go through a drastic decrease in their naturally occurring activity.

The activity of protein function such as enzyme catalysis involves biochemical and biophysical mechanistic aspects. The biochemical mechanism involves interaction between the substrate molecule and residues in the active site of the enzyme. Enzymes function by lowering the activation energy barrier for a chemical reaction. The active site environment provides a complementary structural and electronic environment to the transition state of the catalyzed reaction. A number of other factors have been suggested which can be broadly categorized as biochemical aspects of lowering the activation energy barrier for the catalyzed reaction which include electrostatic effects and providing a hydrophobic environment—which is far different from the solvent surrounded environment. These biochemical mechanisms are part of the "conventional view" depicted in the left panel of FIG. 1. This is the "lock-and-key" model of a substrate fitting into a rigid enzyme.

However, after all the biochemical factors are included there is still a barrier which needs to be overcome by the enzyme catalyzed reaction, and this corresponds to the measured kinetic rate of the protein activity. Typical energy barriers to be overcome require about another 5 to 10 kcal per mole (or even more) of energy. Specialized biophysical features of enzymes provide the energy required to overcome the lowered energy barrier. The ultimate source of this energy is the temperature driven thermo-dynamical fluctuations in the surrounding solvent and environment. For this energy to be transferred into the active site, requires biophysical mechanism of thermodynamical/energetic coupling the distal regions of protein (like the surface loop regions) to the active site. Such a coupling cannot be explained or calculated based on the traditional view of rigid enzymes, instead requires a new view of protein function including enzyme catalysis.

Figure 2:
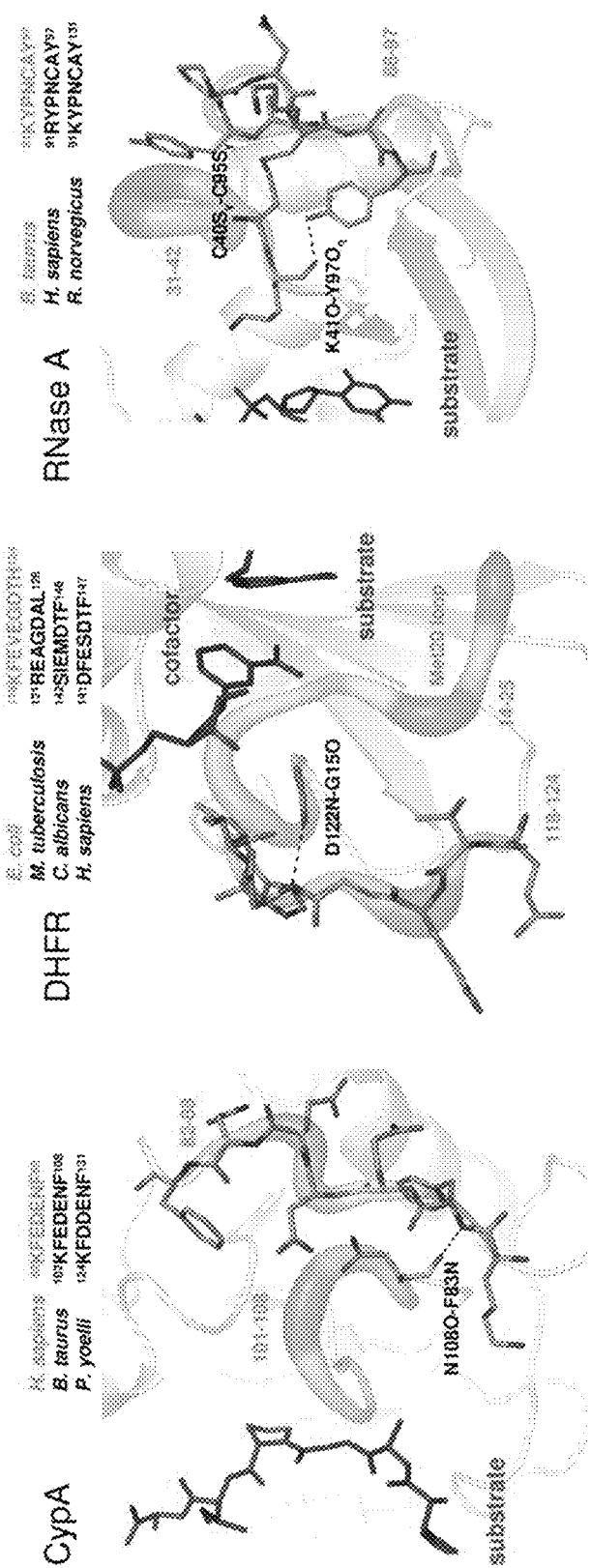
FIG. 2 depicts energy networks present in three different enzyme folds (cyclophilin A, dihydrofolate reductase and ribonuclease A) and biophysical properties of surface sites, identified through the conserved features of the functionally important surface network regions. These networks are conserved features of the enzyme folds and enable function of enzyme by transferring energy from the solvent to the active site.

The new and emerging view of enzyme function involves a flexible enzyme molecule that is able to collect energy from thermodynamic fluctuations of the bulk solvent and the hydration shell solvent and direct it to the active site. The middle panel of FIG. 1 illustrates the energy transfer from the bulk solvent and hydration-shell to the active site. A large number enzymes have already been shown to contain conserved networks of residues that connect surface regions of the enzyme to the active site. Three examples are shown in FIG. 2. These networks provide thermodynamical coupling between the hydration shell, bulk solvent, and the catalyzed reaction. On the surface of the enzyme, the function of these networks is to collect thermodynamical energy from the solvent. Therefore, these regions are highly flexible floppy loops which interact with the solvent. Next to the floppy surface loops are conserved hydrogen bonds and hydrophobic interactions which span the entire enzyme structure and eventually reach into the active site.

These certain surface loops have special biophysical properties. Traditional multiple sequence alignment methods do not recognize any specific patterns of conservations at these sites. However, a detailed characterization of these surface regions indicates the following features, as depicted in FIG. 2. They are dynamic in nature and enable thermodynamical coupling with the solvent. The sequence of these regions does not necessarily contain conserved residue, but instead shows conservation of biophysical property. The biophysical property is optimization of thermo-dynamical coupling with the surrounding solvent. This is accomplished by presence of a large number of residues with long side chains. The side chains on these residues extend out into the solvent, increasing the surface area for the thermo-dynamical coupling. Additionally, these surface regions show energy connectivity to the active site through conserved pathways of residues. The residues in these pathways or networks are connected by hydrogen bonds and hydrophobic interactions to allow the energy transfer from the surrounding solvent into the active site.

The significance of these networks for improving enzymes is illustrated in the right panel of FIG. 1. Once such surface loops of an enzyme are identified that are part of these conserved networks, they can be targeted for improving the energetic coupling between the solvent and the protein residues. For example, one or mutations in these surface regions can be used to enhance the solvent-protein energy coupling, in turn improving the catalytic efficiency. In other applications, partial to complete loop engineering can be done to enable hyper-catalytic enzymes. In yet another application, the information regarding networks and the functionally important surface regions is used to design appropriate immobilization chemistry, in order to avoid degrading the function of these networks and surface regions.

This disclosure specifically describes the identification and characterization of surface sites for enzyme engineering through identification of the enzyme energy networks and identification of conformational sub-states related to the enzyme activity. These energy networks can be identified through a wide variety of experimental and computational methodologies. The basic steps include identification of a series of hydrogen bond and hydrophobic interactions that range from the surface regions of the protein target and span into the active site, and showing direct role in enzyme activity through inspection of the conformational sub-states. In addition to recognition of these linkages, it is also important to verify the biophysical energy connectivity between the surface regions and the functioning or active site of the target.

The identification of the surface sites can be used for carefully designing the immobilization chemistry in order to avoid damaging or hindering these sites. Immobilization is a process where the enzyme is chemically attached to a surface or another material, in order to facilitate reusage of the enzyme or improving the period of application. Immobilization is known to negatively impact the enzyme efficiency. As depicted in FIG. 1, the use of incorrect chemistry that modifies and attaches the enzyme near the surface location of enzyme energy networks hinders the energy flow from the solvent to the active site, thereby impacting the enzyme's activity. The knowledge and location of residues of the enzyme energy networks would allow pre-evaluation of the suitability of the immobilization chemistry to affect these sites.

Once these networks and surface sites are identified using the described methodology and computational approach, they can be ranked for the efficiency of energy flow from the solvent into the active site. This efficiency ranking reflects the ability of the surface site to modulate the enzyme activity.

The identified sites can be engineered in a variety of ways to improve the enzyme activity. In one embodiment, the protein residue at these sites can be mutated to improve the enzyme activity. In another embodiment chimeric constructs can be used and other optimization can be performed to improve the activity by infusing additional kinetic energy and improving its flow into the active site. Surface loops from other enzymes can be incorporated into the sequence of the engineered enzyme to produce a chimeric enzyme. In some embodiments, this chimeric enzyme can incorporate loop sequences from enzymes having similar activity to the target enzyme.

Figure 3:
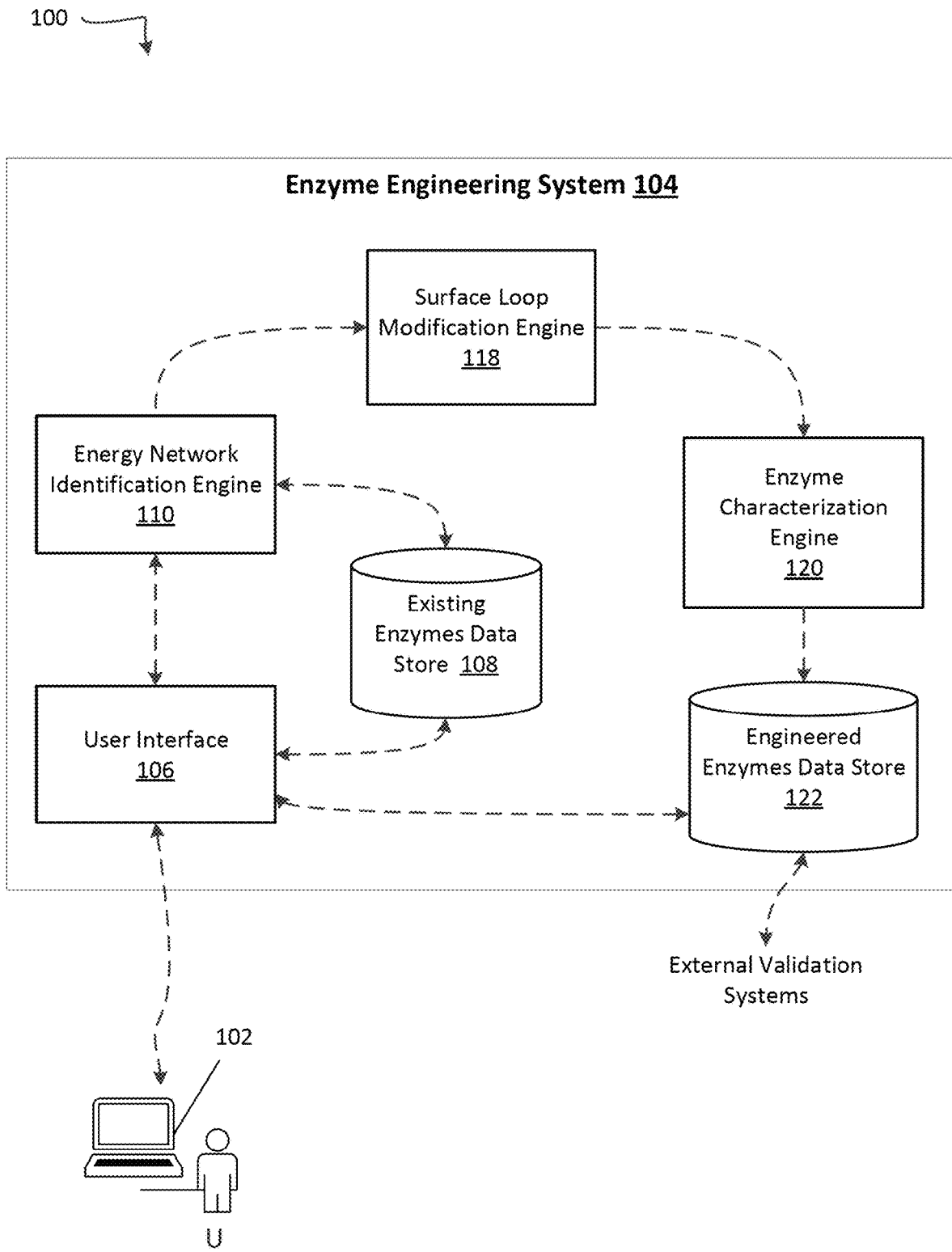
FIG. 3 is a schematic representation of an enzyme engineering system.

FIG. 3 illustrates a schematic diagram 100 of an enzyme engineering system 104 in communication with a computing device 102. The computing device 102 can communicate with the enzyme engineering system 104 through a wired or wireless connection. For example, the computing device 102 could connect to the enzyme engineering system 104 through a network such as the Internet, a local area network, or a Bluetooth connection.

The enzyme engineering system 104 operates to analyze existing enzymes to identify energy transfer networks and modify residues within the enzyme to modify the enzyme's catalytic activity. In some embodiments, the enzyme engineering system 104 includes a user interface 106, an existing enzymes data store 108, an energy network identification engine 110, a surface loop modification engine 118, an enzyme characterization engine 120, and an engineered enzymes data store 122.

The user interface 106 operates to present a display of information in textual and graphical form on the computing device 102. The user interface 106 receives inputs from the user U in the form of selections, text input, and data uploads. In some embodiments, the input is received through an input device in communication with the computing device 102 such as a mouse, keyboard, microphone, or touchscreen. The visual display presents options to the user through the computing device 102. In some embodiments, the options include menus to select enzymes of interest. The user interface 106 also operates to present data to the user U in the form of text, images, tables, charts, graphs, and 3-D models. Inputs received at the user interface 106 can be used to manipulate the data and the displays of the data.

The existing enzymes data store 108 operates to store information about enzymes that can be accessed by the user interface 106 and energy network identification engine 110. The existing enzymes data store 108 includes names of enzymes, structural information about the enzymes, and optionally may also include data on the catalytic activity of enzymes. In some embodiments, if structural data is not available for the enzyme target then structural information from similar members, such as members of same superfamily, is included. In some other embodiments, the existing enzymes data store 108 stores biophysical dynamics data that is obtained by computational analysis of internal movements of the enzyme that affect its designated activity. In some embodiments, this computational analysis is performed using quasi-anharmonic analysis (QAA). In some embodiments, this computational analysis is performed using root-mean-square-fluctuations (RMSF) analysis, principal component analysis (PCA), or normal mode analysis (NMA), or time-averaged normal coordinate analysis (TANCA). In some embodiments, the biophysical dynamics data is obtained by one or more of nuclear magnetic resonance (NMR), X-ray crystallography, cryogenic electron microscopy (Cryo-EM), neutron scattering, and hydrogen-deuterium exchange.

The energy network identification engine 110 operates to analyze biophysical dynamics data for a selected target enzyme to identify potential functionally important sites on the enzyme that are remote from the enzyme's active site. Molecular dynamics simulations are used to analyze different enzyme-substrate complex conformations. Regions of high flexibility on the surface of the enzyme are identified as well as a network of residues connecting these regions to the active site of the enzyme. In some examples, quasi-anharmonic analysis (QAA) is employed to analyze the enzyme conformations. In particular, surface loops connected to the energy networks are identified. In some embodiments, the surface loops include at least 3 residues.

The surface loop modification engine 118 operates to identify surface loops on the surface of the enzyme that are coupled to the active site through an energy network. The top surface loops are analyzed by the surface loop modification engine 118 to identify the best locations within the loop to modify. This analysis takes into account effects of residues on secondary structure of the enzyme. Residues are identified within the loops that can be modified without having a detrimental effect on the secondary structure of the enzyme. Ultimately, the surface loop modification engine 118 generates new sequences of residues for the enzyme including modified surface loops. The resultant engineered enzymes are analyzed by the enzyme characterization engine 120.

The enzyme characterization engine 120 operates to examine engineered enzymes to determine if the desired effect is achieved with the modified amino acid sequence. In some embodiments, the enzyme characterization engine 120 models the engineered enzyme in complex with its substrate using molecular dynamics simulations. In some embodiments, the enzyme characterization engine 120 analyzes substrate kinetics of the engineered enzyme and substrate. In instances where multiple versions of an engineered enzyme are being examined, the enzyme characterization engine 120 can score and/or rank the potential engineered enzymes based on the modeling and kinetics.

The engineered enzymes data store 122 operates to store information about the engineered enzymes. This information can include the results of molecular dynamics simulations and kinetics studies. In some embodiments, the amino acid sequences of the engineered enzymes are stored in the engineered enzymes data store 122. This data store can be accessed by the user interface 106 to display information about the engineered enzyme on the computing device 102. In some embodiments, external validation systems can access the engineered enzymes data store 122 to utilize the information. This information can be used, for example, to construct samples of the engineered enzymes for use in wet lab studies.

Figure 4:
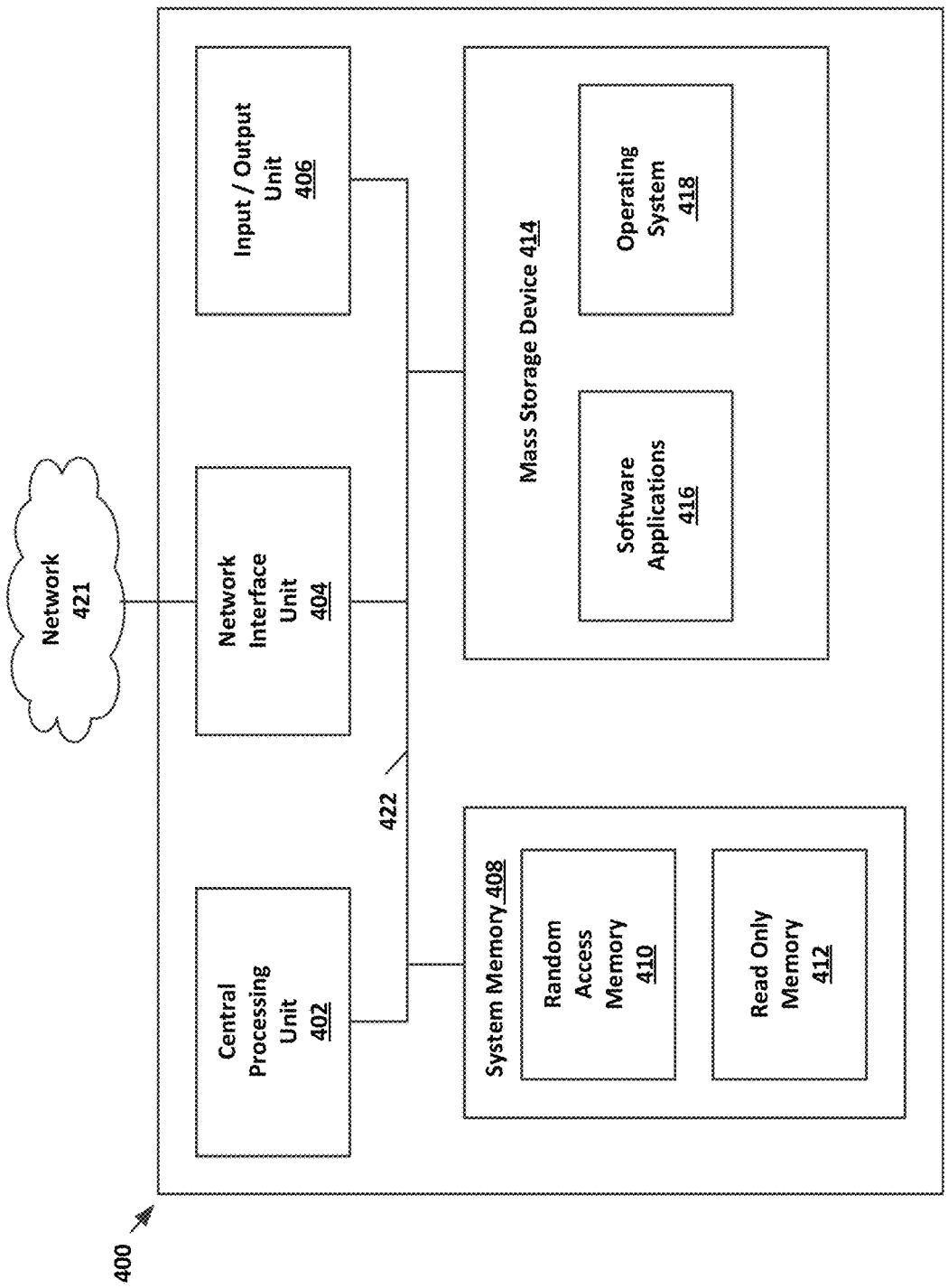
FIG. 4 is a schematic representation of an example computing device usable to implement various aspects of the system of FIG. 3.

FIG. 4 is a block diagram illustrating an example of the physical components of a computing device 400. The computing device 400 could be any computing device utilized in conjunction with the enzyme engineering system 104 such as the computing device 102 of FIG. 3.

In the example shown in FIG. 4, the computing device 400 includes at least one central processing unit ("CPU") 402, a system memory 408, and a system bus 422 that couples the system memory 408 to the CPU 402. The system memory 408 includes a random-access memory ("RAM") 410 and a read-only memory ("ROM") 412. A basic input/output system that contains the basic routines that help to transfer information between elements within the computing device 400, such as during startup, is stored in the ROM 412. The computing system 400 further includes a mass storage device 414. The mass storage device 414 is able to store software instructions and data such as instructions to implement the energy network identification engine 110 or surface loop modification engine 118.

The mass storage device 414 is connected to the CPU 402 through a mass storage controller (not shown) connected to the system bus 422. The mass storage device 414 and its associated computer-readable storage media provide non-volatile, non-transitory data storage for the computing device 400. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 400.

According to various embodiments, the computing device 400 can operate in a networked environment using logical connections to remote network devices through a network 421, such as a wireless network, the Internet, or another type of network. The computing device 400 may connect to the network 421 through a network interface unit 404 connected to the system bus 422. It should be appreciated that the network interface unit 404 may also be utilized to connect to other types of networks and remote computing systems. The computing device 400 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the computing device 400 can store software instructions and data. The software instructions include an operating system 418 suitable for controlling the operation of the computing device 400. The mass storage device 414 and/or the RAM 410 also store software instructions, that when executed by the CPU 402, cause the computing device 400 to provide the functionality discussed in this document. For example, the mass storage device 414 and/or the RAM 410 can store software instructions that, when executed by the CPU 402, cause the computing system 400 to implement the method 500 described in FIG. 5.

Figure 5:
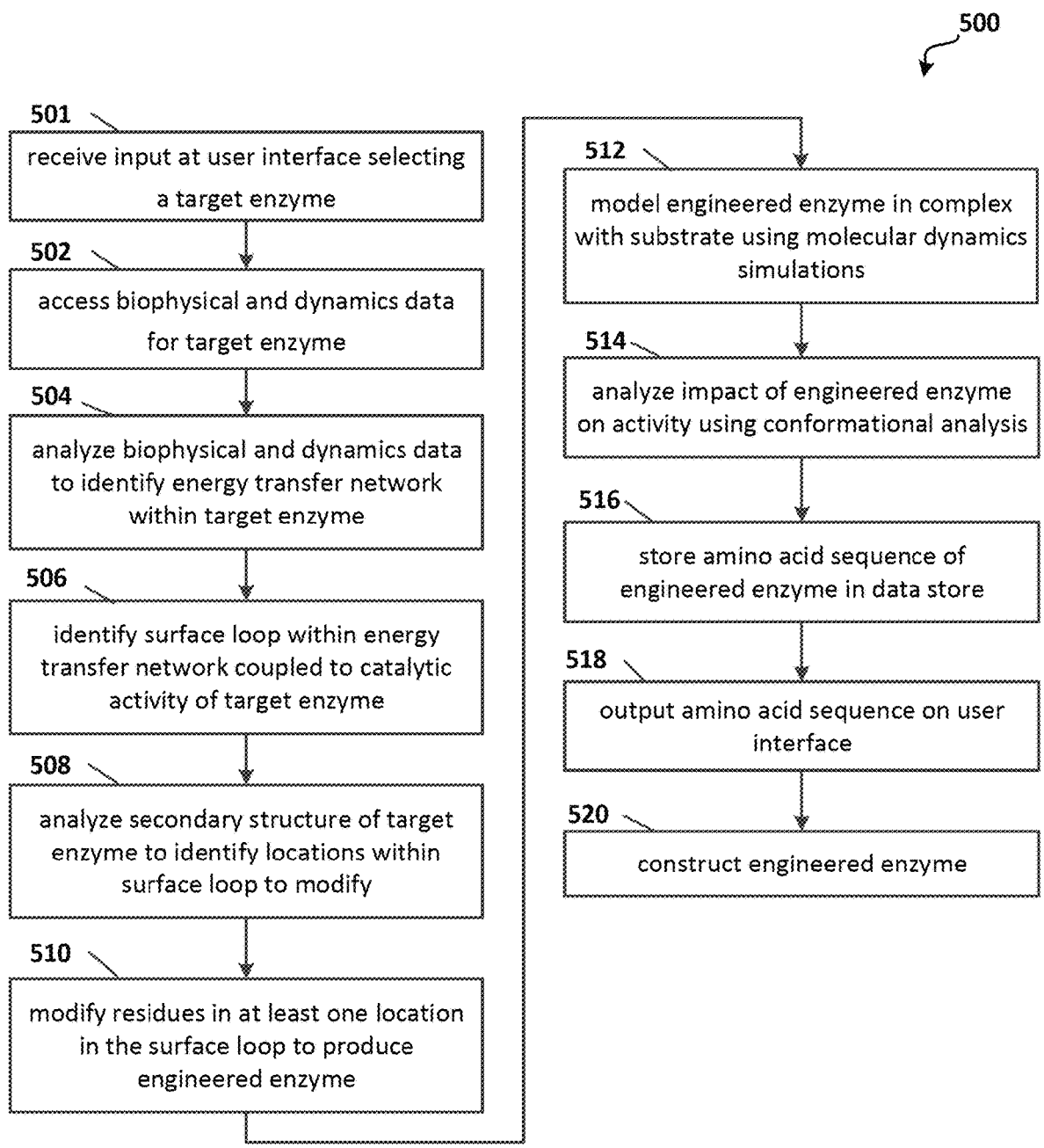
FIG. 5 is a flow diagram illustrating an example method of engineering an enzyme.

FIG. 5 is a flow chart of an example method 500 of engineering an enzyme. In some embodiments, enzymes are modified to enhance their catalytic activity. In other embodiments, enzymes are modified to inhibit their catalytic activity. This method could be performed by the enzyme engineering system 104 of FIG. 3. Other computing systems could be utilized to perform the operations of the method 500. In some embodiments, one or more operations are performed without the aid of a computing device.

At operation 501, input is received at a user interface selecting a target enzyme. The user interface could be the user interface 106 displayed on the computing device 102 operated by the user U. The input could be received by means such as a stylus, a keyboard, a touchscreen, voice input, or a mouse. The target enzyme could be selected from a list or input manually with text or chemical structure input. The target enzyme has a particular catalytic activity of interest. In some embodiments, the target enzyme catalyzes a reaction that is useful for industrial purposes, a medical application or a bench-scale application.

At operation 502, biophysical and dynamics data for the target enzyme is accessed. In some embodiments, the biophysical and dynamics data was previously generated and stored in a data store such as the existing enzymes data store 108. The biophysical and dynamics data is obtained by computational analysis of internal movements of the target enzymes that affect its catalytic activity. In some embodiments, biophysical and dynamics data can be accessed directly from the source of the data, such as computer simulations, experimental techniques and previously published literature.

At operation 504, the biophysical and dynamics data is analyzed to identify energy transfer networks within the target enzyme. An energy transfer network is a series of residues spanning from a surface of the target enzyme to a catalytic site of the target enzyme. Various techniques can be used to analyze protein dynamics including calculating the root-mean-square-fluctuations (RMSF), principal component analysis (PCA), normal mode analysis (NMA), time-averaged normal coordinate analysis (TANCA), quasi-harmonic analysis (QHA), Gaussian network model (GNM), and quasi-anharmonic analysis (QAA). Different sub-states of the molecule's conformations are evaluated to identify regions of high flexibility on the molecule.

At operation 506, a surface loop within the energy transfer network is identified. The surface loop includes residues showing dynamical motions that are coupled to the catalytic activity of the target enzyme.

At operation 508, the secondary structure of the target enzyme is analyzed to identify one or more locations within the surface loop that can be modified. In some embodiments, the surface loop comprises at least 3 residues. In other embodiments, the surface loop comprises at least 5, at least 6, at least 7, at least 8, or at least 9 residues.

At operation 510, the residues within the surface loop are modified to produce an engineered enzyme. In some embodiments, the residues are modified to inhibit the catalytic activity of the target enzyme. In other embodiments, the residues are modified to enhance the catalytic activity of the target enzyme. In some embodiments, at least one residue is inserted into the surface loop. In other embodiments, at least one residue is deleted from the surface loop. One or more residues may also be substituted to change the secondary structure of the loop.

At operation 512, the engineered enzyme is computationally modeled in complex with its substrate using molecular dynamics simulations. In some embodiments, the simulations are used to perform one of root-mean-square-fluctuations (RMSF) analysis, normal mode analysis, (NMA), time-averaged normal coordinate analysis (TANCA), quasi-harmonic analysis (QHA), and quasi-anharmonic analysis (QAA).

At operation 514, the impact of the engineered enzyme with its substrate are analyzed. The impact on conformational sub-states and energy coupling is analyzed.

At operation 516, the amino acid sequence of the engineered enzyme is stored in a data store.

At operation 518, the amino acid sequence of the engineered enzyme is output on a user interface of a computing device. In some embodiments, this is the user interface 106 of the enzyme engineering system 104 that is presented on a display of the computing device 102 in FIG. 3.

At operation 520, the engineered enzyme is constructed using the updated protein sequence of the enzyme. In some embodiments, this is performed by transfecting cells with nucleic acids encoding the engineered enzyme and purifying the engineered enzyme after it is produced by the cells. Once obtained in sufficient quantity, the engineered enzymes can be validated through purification and wet lab experiments. In some embodiments one or more wet lab techniques from spectrophotometric assays, radiometric assays, mass spectrometry, multiple injection method studies, isothermal titration calorimetry studies, stopped-flow kinetics, steady state kinetics, and pre-steady state kinetics measurements are used to evaluate the enzyme activity.

EXAMPLES

Computational Methods for Characterization of Protein Dynamics and Conformational Sub-States Protein dynamics or vibrational modes of a protein are modeled by a set of displacement vectors for each atom in the protein. Several methods are available to compute the vibrational modes of a molecular system such as a protein. A list of suitable techniques for use with the methods and systems described in this disclosure to compute the protein vibrational modes are discussed below.

Normal Mode Analysis (NMA)

This method computes vibrational modes of a molecular system by diagonalization of the Hessian matrix. Assuming the molecular system has N atoms, the Hessian matrix is a 3N×3N matrix. The elements of the matrix are the second order energy derivatives with respect to the displacement of atomic positions in the x, y, z directions. The elements can be computed analytically or computationally. Once the Hessian matrix is computed, it is diagonalized to solve for the eigenvectors and eigenvalues.

$$\varepsilon_i F = \varepsilon_i \omega_i \qquad (\text{Eq. 1})$$

The time-scale of molecular vibration is determined by taking the inverse square root of the eigenvalues ($\varepsilon$) obtained after diagonalization. The eigenvector ($\omega$) corresponding to the eigenvalue represents the vibrational modes, which are a set of displacement vectors for the atoms in the molecular or the protein conformation.

Time-Averaged Normal Coordinate Analysis (TANCA):

This method is similar to NMA in the sense that the protein vibrational modes are obtained by diagonalization of the Hessian matrix. However, NMA suffers from some limitation when considering a highly flexible molecular system such as a protein. NMA uses a reference structure and the eigenvalues and eigenvectors thus obtained are only relevant to the reference starting structure. The method therefore weights highly toward the high frequency motions and less toward the low frequency motions. Moreover, the low frequency obtained using NMA are not reliable for molecular conformations that differ considerably from the reference structure for NMA. In protein function such as enzyme catalysis, the low frequency motions are more important as they are required for overcoming the high energy barriers.

Techniques such as TANCA can partially overcome this problem by diagonalization of the Hessian matrix which has been constructed numerically by averaging the elements over time. This allows the fast frequency motions to be removed by averaging and provides more accurate low frequency modes that are relevant for protein function.

Quasi-Harmonic Analysis (QHA)

This method computes protein vibrational modes from a set of protein conformations that are sampled using either the molecular dynamics (or Monte-Carlo) type simulations. QHA is a powerful method in obtaining vibrational modes that are representative of longer time-scales or the low frequency vibrational, by utilizing the information from a set of structures which may be separated by a long-time scale—or from different parts of the protein conformational space. The vibrational modes are obtained by diagonalization of the atomic fluctuation matrix. For a protein with N atoms, the atomic fluctuation matrix, F is a symmetric 3N×3N matrix with term $F_{\alpha\beta}$ defined as:

$$F_{\alpha\beta} = \langle m_\alpha^{1/2}(x_\alpha - \langle a_\alpha \rangle) m_\beta^{1/2}(x_\beta - \langle x_\beta \rangle) \rangle \qquad (\text{Eq. 2})$$

where $\alpha, \beta$ run through the 3N degrees of freedom in Cartesian space and $m_\alpha$ is the mass of atom corresponding to the $\alpha$th degree of freedom and $x_\alpha$ are the Cartesian coordinates of the atom corresponding to the $\alpha$th degree of freedom. Quantities in <> denote an average determined from molecular dynamics simulation. To obtain the eigenmodes (vibrational modes) diagonalization of the atomic fluctuation matrix is performed (see Eq. 2). The time-scale of protein vibration is determined by taking the inverse square root of the eigenvalues ($\varepsilon$) obtained after diagonalization. The eigenvector ($\omega$) corresponding to the eigenvalue represents the protein vibrational modes, which are a set of displacement vectors for the atoms in the protein confirmation. Note one of the benefits of QHA is that multiple MD trajectories can be combined to construct the atomic fluctuation matrix—thus allowing vibrational modes to be computed that represent conformational changes between different areas of the protein conformational space.

Gaussian Network Model (GNM):

This type of calculation uses coarse-grained normal mode analysis to obtain protein vibrational modes. These calculations use a simple parameter harmonic potential for the particles in the system. The eigenmodes are obtained by the diagonalization of Kirchhoff's matrix, which is similar to Hessian matrix, but uses a reduced model of the protein and treats the protein motions as Gaussian type motions.

Irrespective of the type of method described above, for a protein with N atoms, there are 3N-6 protein vibrational modes. These modes describe a variety of motions within the protein. The modes with fast time-scales indicate repeated movements of atoms, or a small group of atoms that occur as many as a billion to trillion times per second. The intermediate time scales are associated with concerted movements of a group of protein residues. The intermediate time-scales span several orders of magnitude and are associated with motions of loop regions, alpha helices and beta-sheets. The modes associated with the slowest timescales are associated with the overall conformational fluctuations of a protein that involve major domain(s) or even the entire protein. The protein motions at different timescales correspond to kinetic energy to allow overcoming of a variety of energy barriers encountered by the protein in the functional landscape. The fastest motions in the range of $10^{-15}$ seconds to $10^{-12}$ seconds, overcome small energy barriers. The intermediate motions in the range of $10^{-12}$ seconds to $10^{-6}$ seconds are important for overcoming medium height barriers. The slowest motions at scale of $10^{-6}$ seconds and slower (i.e. $>10^{-6}$ seconds) are important for overcoming large energy barriers.

Therefore, using vibrational modes associated with the slowest motions can find conformations within the conformational energy landscape that are separated by high energy barriers. Likewise, the vibrational modes associated with the intermediate and faster motions are useful for inducing more local conformational changes, like the movement of a loop region, an alpha helix, or the side chains of individual residues. Accurate estimates of energy associated with the protein vibrational modes is currently not available, however, the lower estimations would correspond to energy associated with vibrations of individual bonds (<1 kcal/mol) and on the higher end correspond to movement of entire protein domains (5-10 kcal/mol or higher).

Quasi-Anharmonic Analysis (QAA)

This relatively new methodology allows automated discovery of a hierarchy of sub-states associated with the conformational ensemble of proteins. Utilizing atomistic level MD simulations of proteins or protein in association with other molecules (such as binding partners or enzyme-substrate complex) as input, this methodology pays close attention to the anharmonic nature of internal protein motions and pursues the higher-order statistics of the internal motions. One of the most important advantages of this approach is that it allows clean separation between the conformational sub-states, by projecting the conformations sampled during the molecular dynamics simulations in a lower dimensional space represented by QAA vectors. Characterization of the populations in these sub-states for any relevant properties (such as internal energy, distance order parameter, or reaction coordinate) allows the detailed characterization. In addition to identifying these sub-states, the motions associated within the sub-states and inter-conversion between the sub-states provide new insights into the inter-relationship between protein structure, motions and function.

QAA allows characterization of conformational sub-states along a reaction pathway. A hierarchical description of the sub-states along the reaction pathway identifies sub-states with structural and dynamical features critical for attainment of the transition state.

Example 1: Discovering Conformational Sub-States and Surface Sites Associated with Protein Activity QAA was successfully used to organize the complex conformational landscape of the peptidyl-prolyl cis/trans isomerization (PPIase) activity catalyzed by human enzyme cyclophilin A (CypA), into a multi-scale hierarchy of conformational sub-states. The conformational landscape associated with the PPIase activity was sampled using molecular dynamics in combination with umbrella sampling with the isomerized amide bond as reaction coordinate. Over 100,000 conformations collected from the MD simulations were analyzed using QAA.

Figure 6:
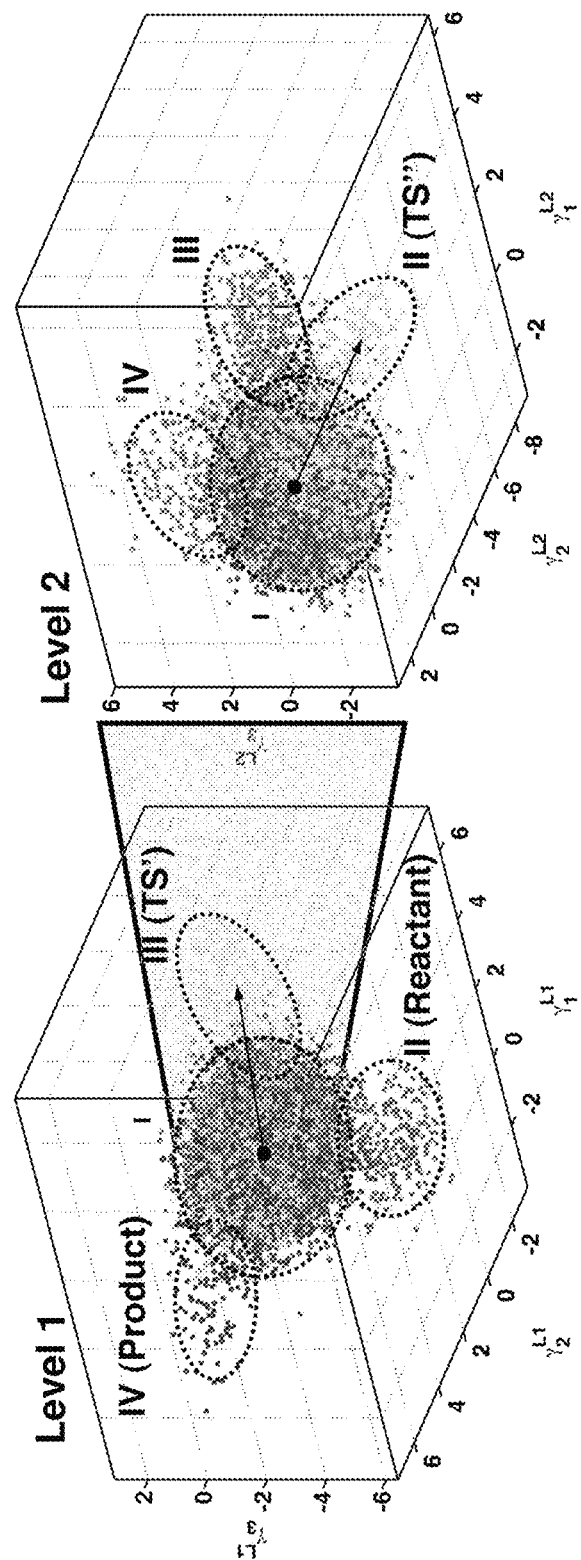
FIG. 6 depicts the use of quasi-anharmonic analysis (QAA) to identify the conformational landscape of cyclophilin A, characterized for peptidyl-prolyl cis-trans isomerization activity. On the left, first round of QAA shows decomposition of the landscape into Reactant (R), Product (P) and Transition State (TS') sub-states. The right panel shows level 2 decomposition performed by taking the mixed conformation sub-state and repeating QAA only on this sub-state.

FIG. 6 shows the results of QAA analysis. On the left, the first round of QAA shows decomposition of the landscape into Reactant (R), Product (P) and Transition State (TS') sub-states. The TS' here is close to but does not correspond to the transition state (TS), which is defined as the highest point on the free energy profile (see FIG. 7). Further analysis of the remaining (mixed) conformations were required to identify the values closer to the true transition state (TS"). Further analysis for Level 2 decomposition is performed by taking the mixed conformation sub-state and repeating QAA only on this sub-state.

Figure 7:
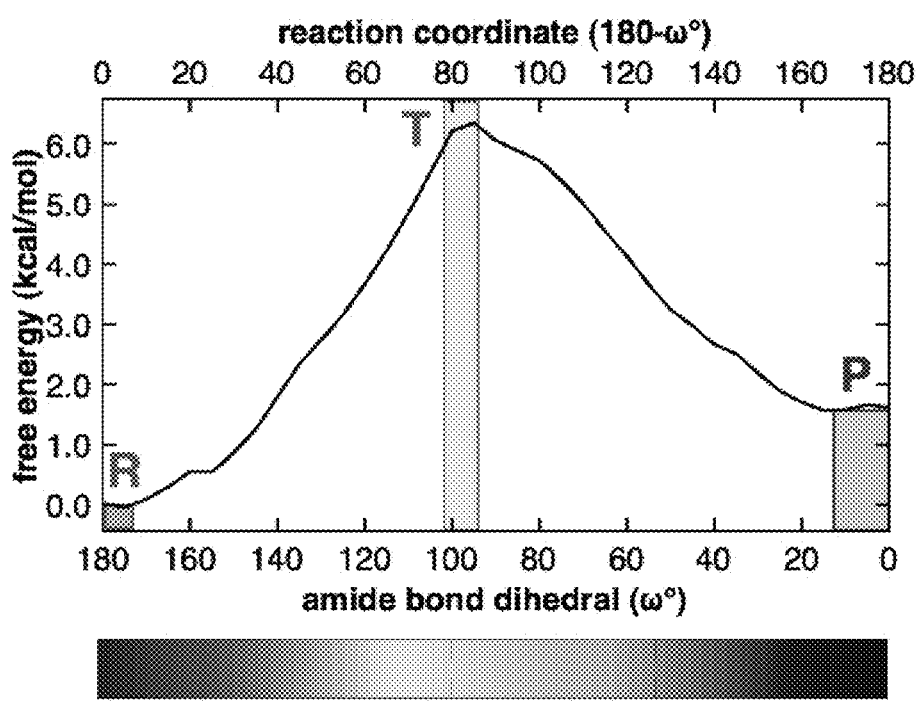
FIG. 7 depicts the free energy profile associated with the peptidyl-prolyl cis-trans isomerization activity of the human cyclophilin A protein. The reaction coordinate is color coded as the reaction proceeds from Reactant (R) state to Product (P) state. The highest point of the free energy profile is defined as the transition state (T or TS).

FIG. 7 depicts the free energy profile associated with the peptidyl-prolyl cis-trans isomerization activity of the human cyclophilin A protein. The amide bond is rotated as the reaction proceeds. The reaction coordinate in this analysis was defined as a value equal to 180—the value of amide bond dihedral angle. The reaction coordinate is color coded as the reaction proceeds from Reactant (R) state to Product (P) state. The highest point of the free energy profile is defined as the transition state (T or TS).

Figure 8:
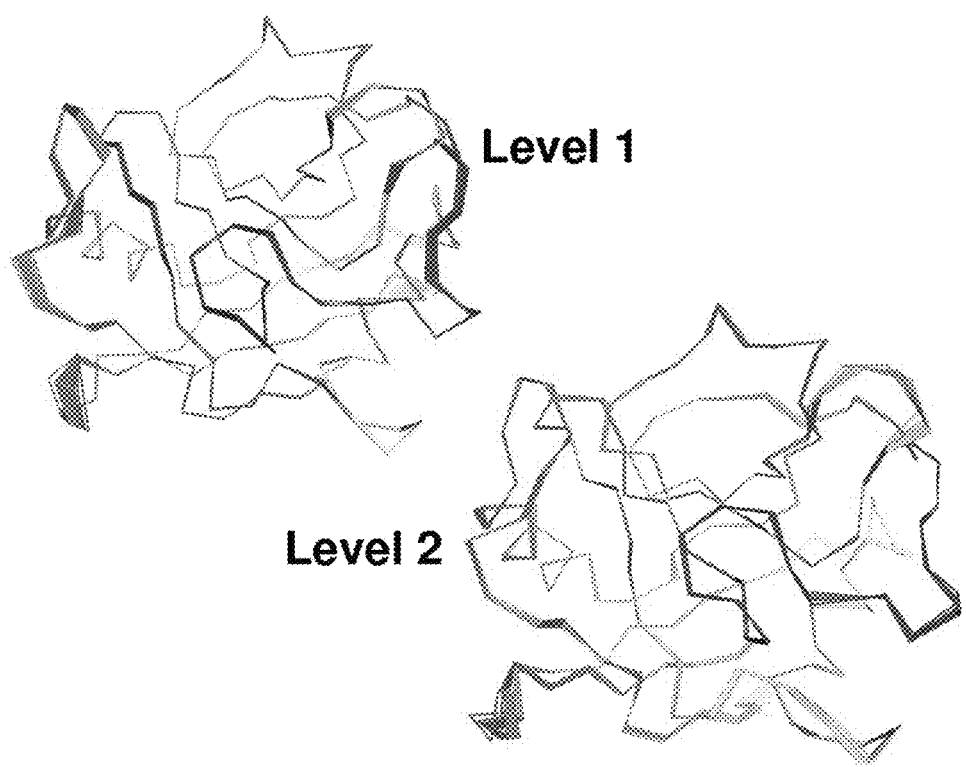
FIG. 8 depicts identification of the conformational changes associated with the protein (human cyclophilin A) as the protein transitions from the ground state into the functionally relevant TS' (Level 1) or TS" sub-state (Level 2).

FIG. 8 depicts identification of the conformational changes associated with the protein (human cyclophilin A) as the protein transitions from the ground state into the functionally relevant TS' or TS" sub-state. The conformational change is depicted in a movie like fashion with only the protein backbone shown. The regions colored are the regions showing largest changes in the conformations. This conformational change corresponds to the black arrows in FIG. 6, as the protein transitions from the central sub-states into the TS' (for Level 1) and TS" (for Level 2) respectively.

QAA allowed identification of independent component analysis (ICA) vectors or modes. The projection of enzyme-substrate complex conformations on the first three dominant QAA modes allows identification of clusters or sub-states (labeled I, II, III and IV in FIG. 6). These sub-states can be characterized for the region of reaction pathway they correspond to by inspecting the reaction coordinate (FIG. 7): reactant, product or near the TS (TS'/TS"). For mixed populations without clear separations into sub-states, the QAA analysis can be repeated in a multi-level fashion (FIG. 6). For CypA, two levels provide qualitative insights as sub-states near TS (the green/yellow colored sub-states TS' and TS") were identified. Protein fluctuations within the sub-states or between the sub-states can be obtained by comparing the changes in protein conformations. For example, the dark black arrows in the figure (both at level 1 and 2) indicate conformational fluctuations associated with enzyme-substrate complex visiting the sub-states TS' and TS" (FIG. 8).

Figure 9:
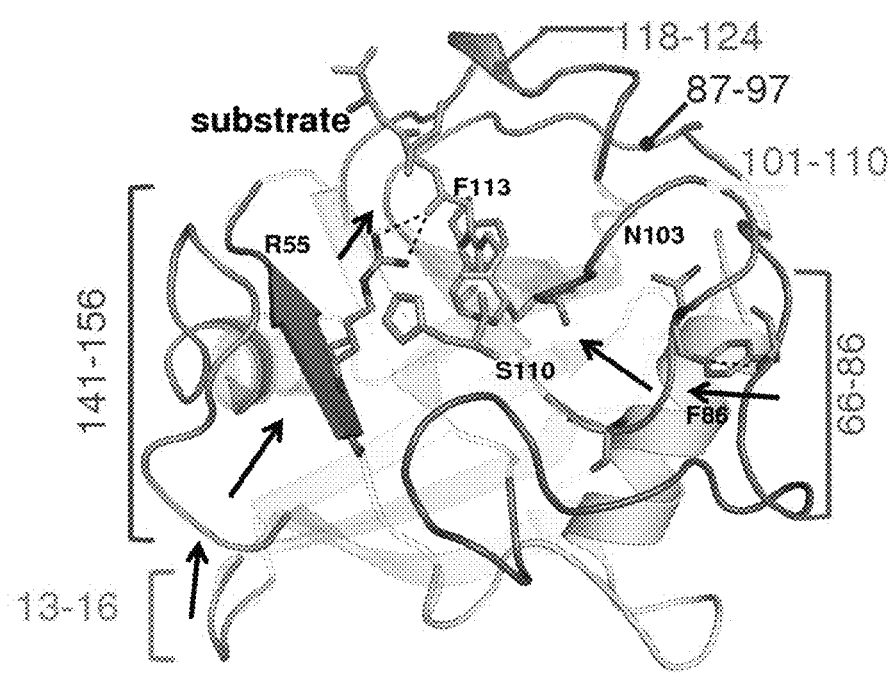
FIG. 9 depicts identified surface loops and pathways in human cyclophilin A connecting these surface loops to active site.

FIG. 9 depicts identified surface loops and pathways in human cyclophilin A connecting these surface loops to active site. These conformational changes associated with the protein as is transitions into the functionally relevant sub-state associated with the peptidyl-prolyl cis-trans isomerization activity (shown in FIG. 6 and FIG. 8) allowing the identification of these surface regions and the network pathways which connect them into the active site. Any changes on these surface loops will have impact on the protein activity, therefore, these surface regions would serve as sites for controlling this protein's activity through engineering.

Figure 10:
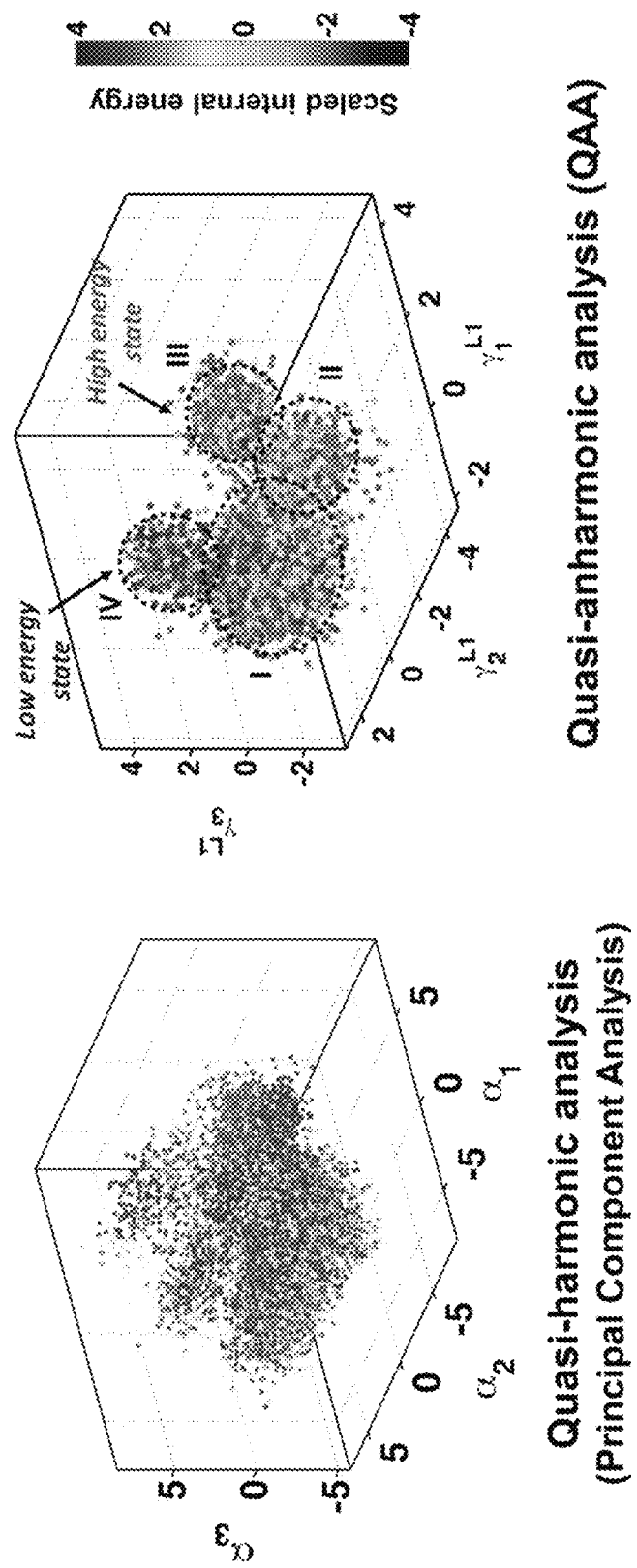
FIG. 10 depicts the unique benefit of using the approach quasi-anharmonic analysis (QAA) versus other approaches such as principal component analysis or quasi-harmonic analysis (QHA). QAA provides clear identification of homogeneous conformational sub-states. The results shown are from protein human ubiquitin and the coloring is based on scaled conformational (internal) energy. The conformations were obtained from molecular dynamics simulations.

FIG. 10 depicts the unique benefit of using the approach quasi-anharmonic analysis versus other approaches such as principal component analysis or quasi-harmonic analysis. The same conformational landscape when subjected to the analysis based on these different method gives different results. The QAA approach identifies the correct conformational sub-states of high and low energy while the other approaches do not provide clear separation into homogenous sub-states. The results shown are from protein human ubiquitin and the coloring is based on scaled conformational (internal) energy. The conformations were obtained from molecular dynamics simulations.

For CypA, the enzyme fluctuations that allow visiting the TS' and TS" correspond to the motions of previously identified network promoting catalysis (FIG. 9). Detailed characterization of the motions that lead to the sub-state (TS'/TS") identified regions of high flexibility on the surface and the network of residues connecting these regions to the active site (FIG. 9). The list of network residues is similar to the results obtained from different techniques including NMR spectroscopy and other computational results.

Overall, these results indicate that QAA allows the identification of the conformational sub-states associated with enzyme activity of a protein. Detailed analysis of the functionally relevant conformational sub-states allows the identification of rate limiting conformational transitions that allow access into these sub-states. Further structural analysis of these sub-states and conformational transitions allows the identification of surface regions of the enzyme with large dynamical motions on the surface, and the network of residues that connect these surface regions to the active site.

Ranking of Surface Sites and Networks Based on Energy Flow

Once discovered the surface sites can be assigned a score for their ability to control the target activity. Based on the assigned score, the ranking of these surface sites could serve as an important metric in enzyme engineering efforts. Engineering a surface site with little or no impact on protein activity would lead to loss of time and effort. Therefore, it is important to assign a score or ranking of each discovered surface site for their impact on enzyme activity. In other efforts, already discovered target engineering sites can also be assigned an energy transfer or coupling score as a metric for its ability to control target activity.

In one approach, to obtain the efficiency of energy flow within proteins, an information theoretic approach can be used in combination with molecular dynamics simulations. In this approach the ability of protein residues (or atoms) to participate in energy flow is investigated by observing its ability to receive and pass a "signal" to its neighbors. The localized neighbors can include solvent (if the atom is exposed to the solvent), ions, and other protein atoms. Using the frequency of the number of times a residue makes contact with another residue (either via hydrogen bonding or van der Waals contact) the expected time for a "signal" to propagate from one residue (for example located on the surface of the protein) to another residue (for example located in the active site) can be computed. In information theory, this expected time of signal propagation within a network is investigated using hit times, which can also be used to estimate how a protein may communicate with its neighbors. The methodology to compute hit times has been previously described elsewhere.

Figure 11:
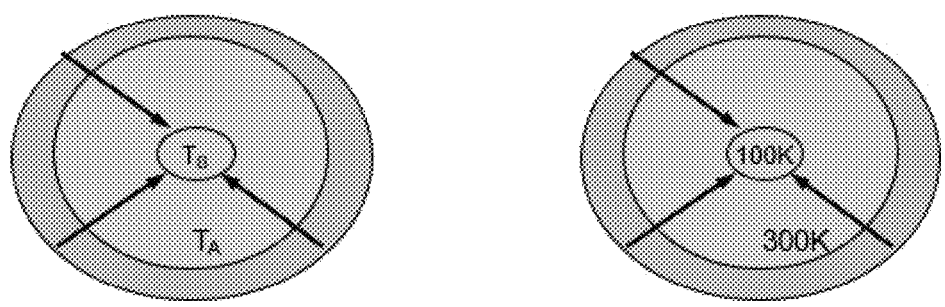
FIG. 11 is a schematic diagram illustrating energy flow within a protein as a result of a temperature gradient.

In another approach to calculating the efficiency of energy transfer, conductance of energy flow along various atom-atom contacts is calculated using data from molecular dynamics simulations. Molecular dynamics simulations provide atomic coordinates and velocities associated with each atom as the systems evolves. Conductance of energy is calculated using the coordinates and velocity information. In regular molecular dynamics systems, a constant system temperature is maintained throughout the system. However, to investigate the preferential pathways of energy flow through the protein a gradient of energy is created between two different parts of the system as depicted in FIG. 11.

In this example, to investigate the energy flow between the protein surface and active site, the simulations can be performed at temperature $T_A$ while the active site is kept at a lower temperature $T_B$. The left panel of FIG. 11 shows that a temperature of $T_A$ is used for the simulation of enzyme assembling including the solvent, while $T_B$ is used for the active site. The lowering of temperature is performed by reassigning the atomic velocities at a predefined number of steps. This results in creating an energy gradient and inducing a result energy flow into the active site. In the right panel of FIG. 11, the sample temperature values used were $T_A$=300K and $T_B$=100 K.

Any two atoms in contact will have a slightly different temperature due to the temperature gradient. Two atoms are deemed to be in contact if their distance in the native conformation, $r_{ij}^{NAT}$ satisfies the condition $$r_{ij}^{NAT} < \sigma_i + \sigma_j + 1/2(\delta r_i + \delta r_j) \quad \text{(Eq. 3)},$$

where $\sigma_i$ is the van der Waals radius of atom i and $\delta r_i$ is the standard deviation for the distribution of displacements of atom i from the average conformation. The heat flux flowing from atom i to atom j can then be estimated with an expression analog to Fourier's law, $$J_{i \to j} = w_{ij} k_B (T_i - T_j) \quad \text{(Eq. 4)}.$$

$T_i$ is the temperature of atom i, determined from its time-average kinetic energy via $$3/2 k_B T_i = 1/2 m_i \langle v_i^2 \rangle \quad \text{(Eq. 5)}.$$

The heat transmission frequency $w_{ij}$ between atoms i and j is derived from the corresponding element of the covariance matrix of the mass-weighted atomic displacements from the average conformation, $$w_{ij}^2 = \left| \frac{k_B (T_i + T_j)}{\langle m_i^{1/2} \delta \vec{r}_i \cdot m_j^{1/2} \delta \vec{r}_j \rangle} \right|. \quad \text{(Eq. 6)}$$

Once interatomic fluxes are computed, fluxes between any two residues R and R' can be obtained by adding up interatomic fluxes between pairs of atoms, $$J_{R' \to R} = \sum_{i \in R'} \sum_{j \in R} J_{i \to j}. \quad \text{(Eq. 7)}$$

The energy conductance of residue R is defined as the sum of all heat fluxes entering and exiting the residue, $$C_R = \sum_{R'} |J_{R' \to R}|. \quad \text{(Eq. 8)}$$

Residues with a high energy conductance are thus important in channeling the energy flowing from the solvent towards the reaction center where the energy-sink atoms are located. The obtained information of energy conductance is used two ways for surface site of energy channels to be scored and ranked. First, the values of $C_R$ associated with each network residue are tabulated. Second, each network is assigned an overall score and ranking; with ranks assigned based on scores ordered from largest to smallest. The network pathway score in its simplest form is an average of $C_R$ values of the network residues; therefore a network consisting of residues with high $C_R$ values will show higher score of energy transfer efficiency. In another embodiment a multiplicative score is used to assign the overall score for the network ($C_R$ values of all network residues are multiplied). In another embodiment, if no information about the surface sites is available then residues showing high $C_R$ values are connected and inspected further for the existence of the network and surface sites.

Example 2: Energy Efficiency Scoring $NADP^+$ binding proteins play important roles in cellular redox reactions. A number of these proteins have been investigated widely for presence of protein residue networks associated with their activity. These include investigations of enzyme dihydrofolate reductase (DHFR) from *Escherichia coli* (EcDHFR), *Mycobacterium tuberculosis* (MtDHFR), *Candida albicans* (CaDHFR) and humans (hDHFR). These enzymes catalyze the transfer of hydride between the $NADP^+$ cofactor and a substrate. Conserved networks have been identified in each of these enzymes. To investigate the energy flow and conductance along the networks, a combination of MD simulations was used with the developed methodology.

MD simulations were performed that add small amounts of excess kinetic energy in different areas of the protein surface and then monitor the energy flow from these areas into the active site. As depicted in FIG. 11 this was done to keep the active site at 100 K while the remaining enzyme and solvent was kept at 300 K.

MD simulations were carried out near equilibrium in a quasi-steady state. Every 1 picosecond (ps), velocities from a subset of atoms in the immediacy of the hydride transfer reaction site were rescaled such that the total kinetic energy is decreased by 9.552 kcal/mol. These atoms are termed the energy-sink atoms. The selected amount of energy extracted is such that would result in an immediate cooling of the energy-sink atoms to a final temperature of 100 K, provided the atoms were at an initial temperature of 300K. This energy decrease is high enough to provide a signal above thermal noise. The extracted energy is immediately transferred to the solvent by rescaling solvent atom velocities. An amount of energy equal to 9.552 kcal/mol divided by the total number of water molecules is added to every water molecule. As a result of repeating this energy redistribution every 1 ps, a heat flux converging towards the protein and approximately constant for time scales >>1 ps arises. A net flow of heat enters the protein through the surface residues and makes its way to the energy sink atoms, and then back to the solvent ending the cycle. Simulations were carried out for a total of 200 ps.

In addition to the heat flux, a temperature gradient within the protein is formed such that the energy-sink atoms have an average temperature of about 100 K, while the protein atoms far from the energy-sink atoms and in contact with the solvent have an average temperature of about 300 K.

Figure 12:
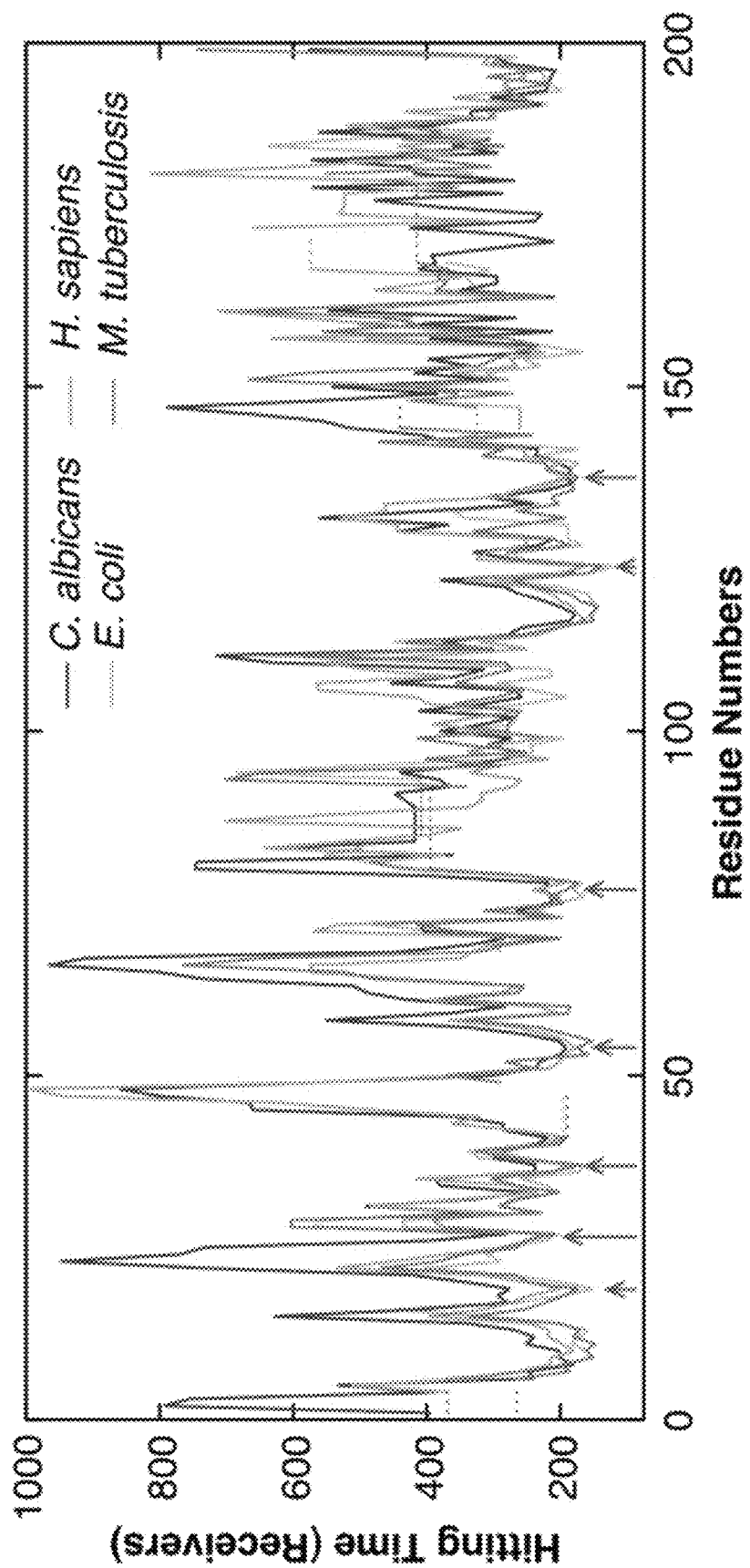
FIG. 12 is a line chart showing hit time plotted against residue numbers for dihydrofolate reductases (DHFRs) from the four different species: *Escherichia coli, Mycobacterium tuberculosis, Candida albicans* and human.

EcDHFR structure shows preferential pathways for energy flow that enables coupling of hydration shell solvent with the active site. The informatics approach indicates certain residues are better at communicating with other residues. The list of residues includes Ala7, Ile14, Phe31 and Tyr100 and shows lowest hit times (as depicted in FIG. 12). In this informatics approach, hit time is a measure of time (in arbitrary units) that it takes each residue to communicate a message to its neighbors. Residues with lowest hit times are therefore indicate residues that are most suitable at relaying long-distance communications. An overall inspection of the EcDHFR structure shows that the external loop shows low hit times while the internal residues show higher hit times. These residues with low hit times have been previously indicated to a part of conserved network of coupled motions. Although it is useful in identifying these residues that are suitable for long range communications in enzyme structures, the informatics approach does not provide insights into the biophysical mechanism of long-range connectivity.

The biophysical mechanism of long-range connectivity was tested by monitoring energy flow within the enzyme structure. It has been previously suggested that the energy flow in protein structure may be a possible mechanism for long range communications. Using an approach previously designed where a temperature gradient is introduced to induce energy flow from one region of the molecular system to another, the flow of kinetic energy was monitored from the solvent to the active site residues. A small number of atoms in the active site were cooled (by scaling down the atomic velocities in molecular dynamics run periodically), while the entire system was kept at constant temperature of 300 K. The cooling of atoms in the active site is motivated by treating the active site as a sink of energy, where the energy facilitates in overcoming the free energy of activation. With this temperature gradient in place during the hydride transfer reaction, the ability of residue pairs in enzyme-substrate to conduct kinetic energy was characterized. This allowed computation of energy connectivity of each residue in the protein. Higher values of the energy connectivity indicate that the residues are more suitable for conducting the kinetic energy from solvent on the enzyme surface into the active site.

Figure 13:
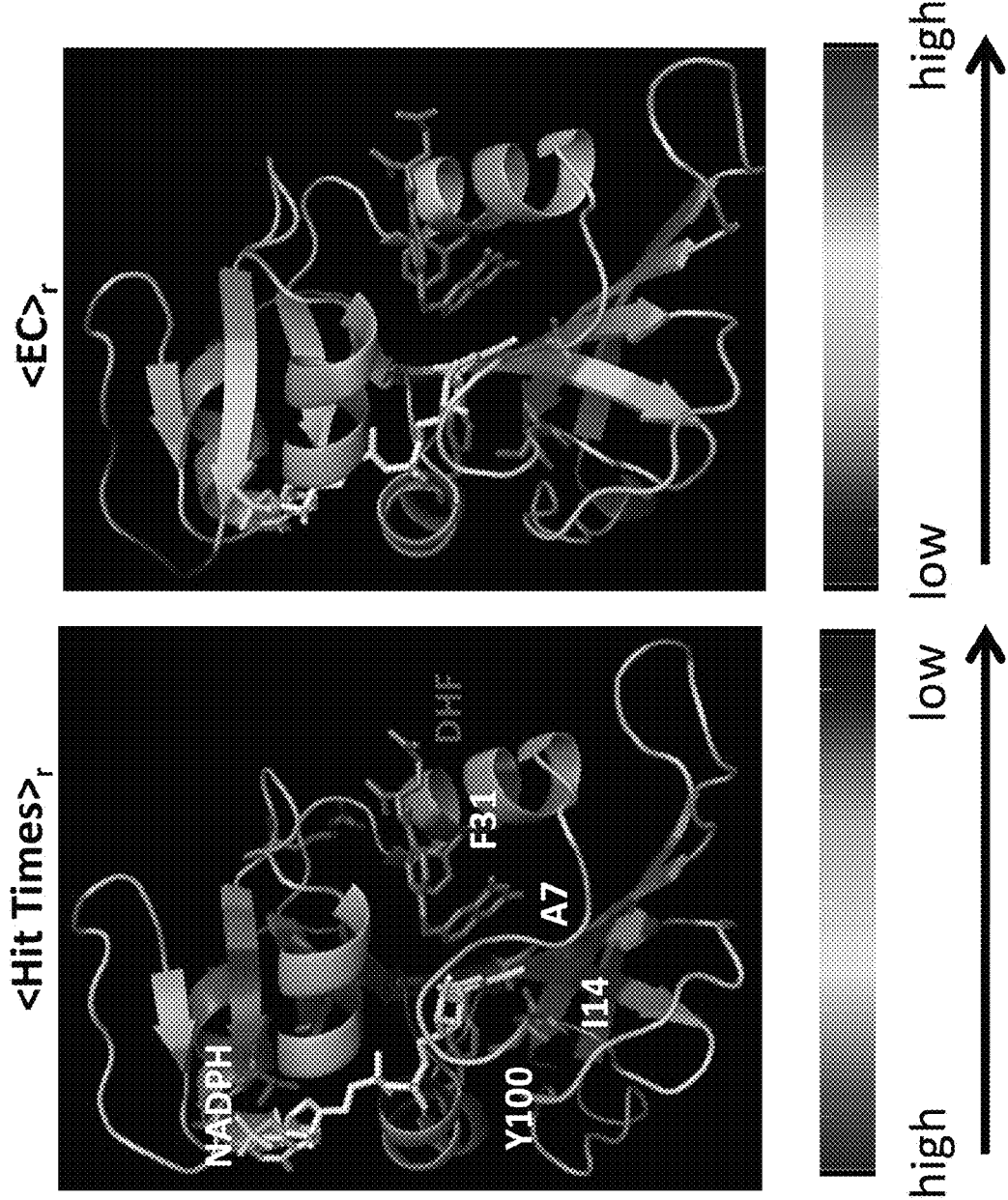
FIG. 13 depicts the results obtained for the hit times and energy conductance values for the *E. coli* dihydrofolate reductase (EcDHFR).
Figure 14:
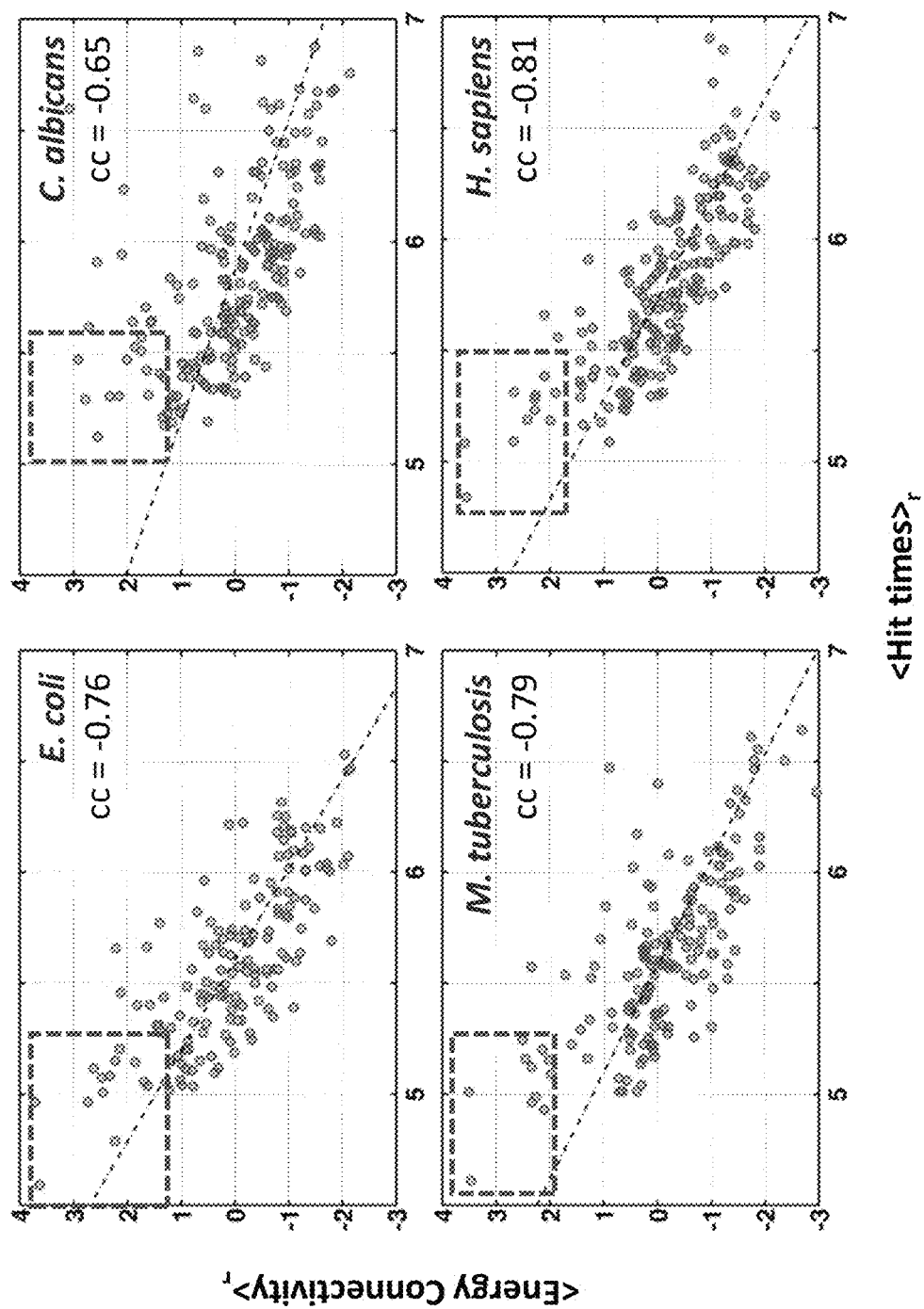
FIG. 14 depicts the inverse correlation between hit time and energy conductance. Energy conductance is a measure of a residues ability to relay energy to its neighbors. The network residues (with low values of hit times and high energy connectivity) from DHFR are indicated with the dashed rectangle for each of the four species *Escherichia coli, Mycobacterium tuberculosis, Candida albicans* and human
Figure 15:
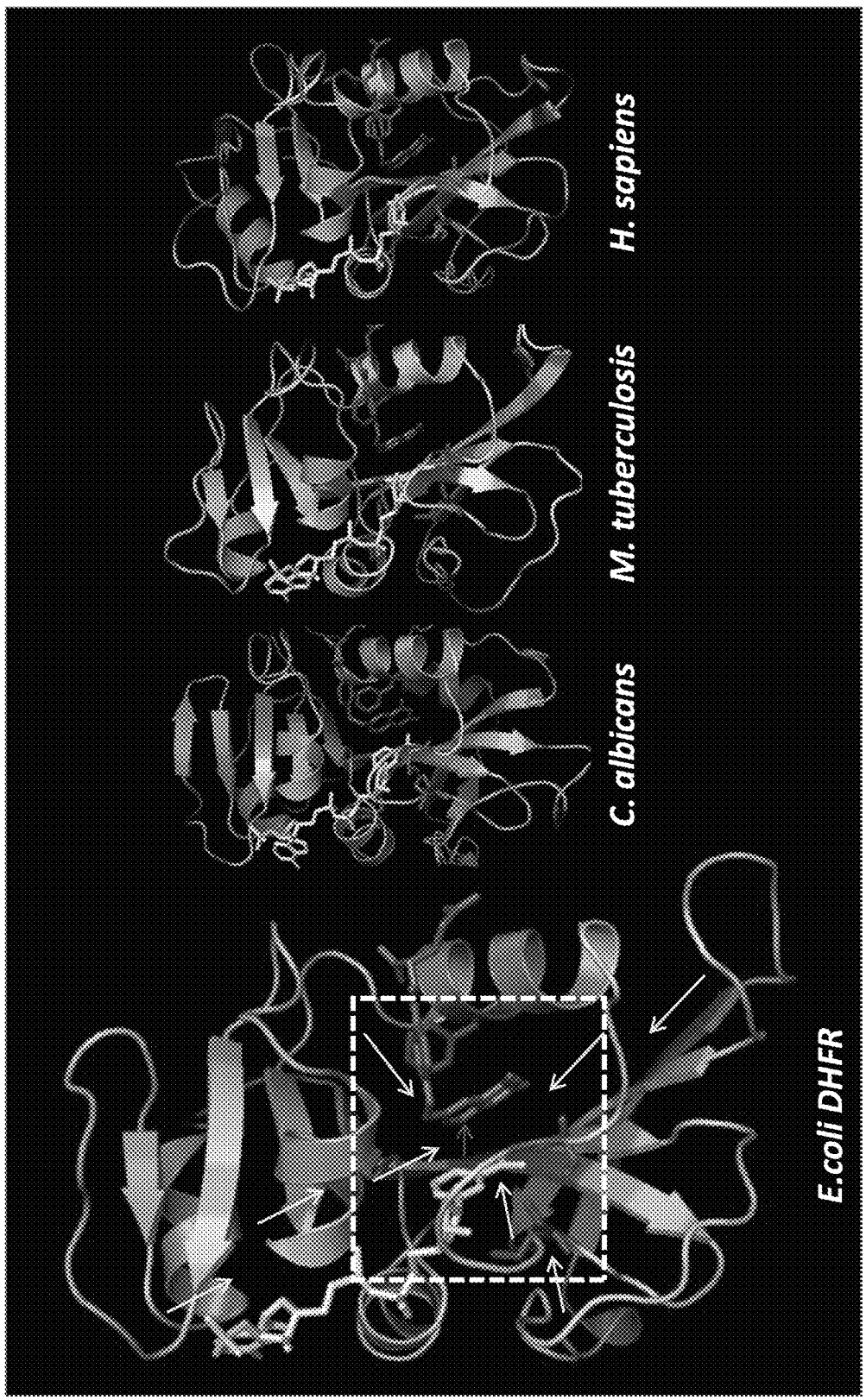
FIG. 15 depicts the results of the energy conductance for dihydrofolate reductase from the four species: *Escherichia coli, Mycobacterium tuberculosis, Candida albicans* and human. The arrows indicate the flow of energy from the surface to the active site.

The two approaches provide quantitatively similar results as depicted in FIG. 13. Correlation indicates that residues with low hit times are good at conducting energy. For EcDHFR, the residues with the best ability to conduct energy same as the ones have been previously implicated in network of coupled motions. Active site residues that participate directly in enzyme mechanism are known to be conserved; however, role of conserved residues located distal to the active site still remains a mystery. Therefore, DHFR structures from the other three different species were also examined with the same approaches (FIG. 14 and FIG. 15).

Results indicate that the residues which are most suitable for long range energy connectivity are conserved across evolution. These 4 species share only 30% sequence similarity. It is important to note that the simulations used for computing energy connectivity were performed in non-equilibrium conditions as an artificial energy gradient was introduced by cooling the active site. The simulations used in the informatics approach were performed under equilibrium conditions, with no temperature gradient or any other constraints on the systems. Therefore, both of these approaches for identifying the same residues provides confidence in the ability to characterize the residues for long range connectivity in proteins.

The results from the informatics and the biophysical approach can be summarized as follows. The enzyme structure shows presence of conserved residues, all the way from surface to the active site, that provides channels of long-range connectivity. The flow of energy from the surrounding solvent on the enzyme surface through these channels into the active site is the mechanism of the long-range connectivity. It is hypothesized that this energy is required to overcome the activation energy barrier in the active site. The residues that form these conserved channels have been indicated to be part of conserved networks.

Further these two approaches allow providing a quantitative score to each residue (hit time and energy connectivity) which is used to evaluate the ability of the residue to transfer the energy from surface to the active site.

Example 3: Engineering Butyrylcholinesterase (BChE) Surface Loop for Improving Function Improved therapies to counteract the toxicity of organophosphorus (OPs) anticholinesterases have been sought for decades. OPs are commonly used as insecticides. The OP nerve agents such as sarin (2-[fluoro(methyl)phosphoryl]oxypropane) also act as potent anticholinesterases and are some of the most toxic synthetic chemicals ever created.

Bioscavengers for OP anticholinesterases are proteins that bind to and inactivate the toxicants in the circulation before they can reach systemic target organs to elicit cholinergic toxicity. There are two types of bioscavengers: stoichiometric and catalytic. While stoichiometric scavengers bind OP molecules in a near 1:1 ratio, catalytic scavengers can reactivate following phosphylation by the OP, making them potentially much more efficient. Enzymes which catalyze OPs naturally (e.g. organophosphorus acid anhydrolase, paraoxonase, phosphotriesterase) have been purified and tested but often suffer from issues such as low catalytic rate, limited substrate selectivity and immunogenicity.

The stoichiometric bioscavenger enzyme butyrylcholinesterase (BChE) has essentially no effective catalytic rate with any OP substrates but exhibits a widespread binding affinity for many OPs. Moreover, it has been demonstrated to be safe and effective with little immunogenicity at high doses. Due to its stoichiometric interaction with an OP, however, a very large dose of the enzyme is required, leading to practical problems with its use as a prophylactic agent.

Kinetically, OPs interact with BChE in a manner similar to choline esters. A Michaelis complex is initially formed (described as the ratio of association vs dissociation, $k_1/k_{-1}$) which rapidly progresses to acylation (in the case of choline ester) or phosphylation (in the case of an OP, $k_2$). The subsequent kinetic step ($k_3$) is markedly different between choline and OP substrates. In deacylation, a histidine-bound water molecule rapidly displaces the acyl group from the catalytic serine residue in the active site. In dephosphylation, the histidine-bound water molecule is sterically hindered from displacing the phosphorus atom, thus it remains covalently attached to the active site serine. While rapid deacylation with a choline substrate allows return of the enzyme to an effective catalyst, the slow dephosphylation step leaves the catalytic reaction blocked, leading to accumulation of the endogenous signal acetylcholine leading to cholinergic toxicity.

Previous work identified a BChE mutant ($BChE_{G117H}$) with a marked increase in reactivation with a number of OPs. The mutation G117H is required for the catalytic activity of OPs hydrolysis. Despite showing increased catalysis compared to the native enzyme, the turnover rate of $BChE_{G117H}$ ($k_{cat}$=0.75 min$^{-1}$) remained much too low to be an effective catalytic scavenger in vivo. An emerging concept in enzyme function is that dynamic motions of peptide sequences on an enzyme's surface, distant from the active site region, can influence the rate of a catalytic reaction. It has been proposed that catalytic rate is affected by thermodynamical coupling of the hydration-shell, the bulk solvent, and the catalyzed reaction. For a number of enzyme systems, networks of conserved residues have been discovered that span from the surface of the protein to the active site region, effectively coupling with the catalytic reaction mechanism. In fact, enhancing energy flow through these networks may be a general approach for increasing enzyme-mediated catalysis.

It is proposed that within limits, energy transfer from the surface loop to the catalytic site is influenced by the sequence, quantity and physicochemical nature of the peptides within the network. Thus, increasing the length of this loop and facilitating its interaction with the solvent is hypothesized to increase catalytic activity by increasing energy transfer. It was hypothesized that applying these principals to $BChE_{G117H}$ would aid in the development of a rationally-designed mutant with increased catalytic activity towards OPs.

Figure 16:
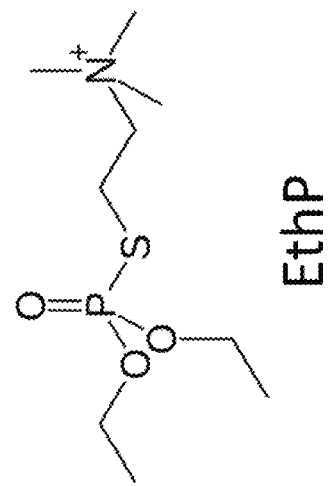
FIG. 16 depicts the structures of organophosphate (OP) anticholinesterases compounds (paraoxon, PO; diisopropylfluorophosphate, DFP; echothiophate, EthP) used for investigation of engineered butyrylcholinesterase (BChE) activity.
Figure 16:
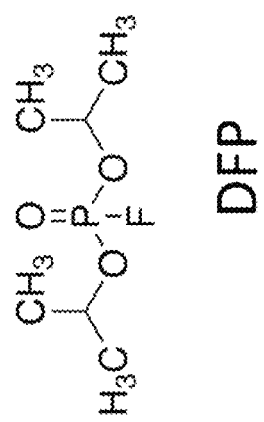
Figure 16:
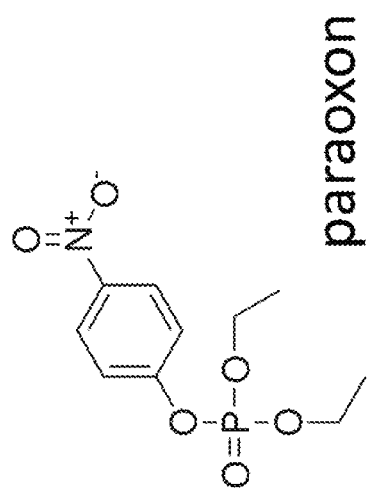

FIG. 16 shows the chemical structures of the three OPs studied. Paraoxon (O,O'-diethyl-p-nitrophenyl phosphate), 98.6% purity) was purchased from ChemService (West Chester, Pa.). A 10 mM stock solution of paraoxon was prepared in 100% dry ethanol and kept desiccated under nitrogen at −80° C. until use. Diisopropylfluorophosphate (2-[fluoro(propan-2-yloxy)phosphoryl]oxypropane), >99%) was stored at −80° C.[23].

Computer Simulations and Analysis

Molecular dynamics (MD) simulations were performed to model native and engineered $BChE_{G117H}$ in complex with OP (PO, EthP and DFP) and choline (butyrylcholine, BCh) substrates in explicit water solvent. Note that the native enzyme considered for all modeling studies includes the G117H mutation, as it is required for catalytic activity. Model preparation and simulations were performed using the AMBER v14 suite of programs for biomolecular simulations (ambermd.org). AMBER's ff14SB force-fields were used for all simulations. The parameters for the substrates were obtained using the protocol described in the AMBER manual. MD simulations were performed using NVIDIA graphical processing units (GPUs) and AMBER's pmemd.cuda simulation engine.

A total of twenty-four separate simulations were performed, based on the combination of native and engineered versions of $BChE_{G117H}$ in complex with PO, DFP and EthP, as well as with BCh. The enzyme was modeled based on the coordinates available in the protein data bank (PDB ID: 4BDS). The substrates were modeled based on the diester substrate coordinates for acetylcholine coordinates (PDB ID: 2ACE), the template for the diester bond was used and the remaining crystal structure and the atoms were added by AMBER's leap program based on the substrate template developed using AMBER's protocol.

After processing the coordinates of the protein and substrate, all systems were neutralized by addition of counterions and the resulting system were solvated in a rectangular box of SPC/E water, with a 10 Å minimum distance between the protein and the edge of the periodic box. The prepared systems were equilibrated.

The equilibrated systems were then used to run 200 nanoseconds (ns) of production MD under constant energy conditions (NVE ensemble). The production simulations were performed at a temperature of 300 K and a time-step of 2 femtoseconds (with SHAKE algorithm applied to bonds and angles involving hydrogens). As NVE ensemble was used for production runs, these values correspond to initial temperature at start of simulations. Temperature adjusting thermostat was not used in simulations; over the course of 200 ns simulations the temperature fluctuated around 300 K with RMS fluctuations between 2-4 K, which is typical for well-equilibrated systems. A total of 10,000 conformational snapshots (stored every 20 ps) collected for each system was used for analysis.

Modeling the Hydrolysis Reaction

Standard MD simulations (described above) can only model fixed electronic states, and thus chemical reactions cannot be modeled. To characterize the protein dynamics associated with the hydrolysis step, a simple 3-state model was used. The reaction was modeled using a product, transition state and product state. The transition state was modeled based on the previous acetylcholinesterase studies. Three separate MD simulations (based on the protocol described above) were performed for each of these states. However, the production run for these simulations was 100 nanoseconds. These simulations were only performed for G117H with paraoxon as a representative OP substrate.

Calculations for Protein Dynamics

Quasi-anharmonic analysis was used to analyze the conformational landscape associated with the BChE activity. Furthermore, the aggregated root-mean-square-fluctuations for top 10 quasi-harmonic modes ($RMSF_{10}$) were used to calculate protein flexibility. It is well known that the slowest 10 modes contribute to the majority of fluctuations in proteins (>80%) and the use of $RMSF_{10}$, instead of all modes, removes the faster stochastic motions of the protein, allowing focus on intrinsic dynamics of proteins. Both these calculations were performed using AMBER's ptraj analysis program. All trajectory conformations were first aligned to a common structure, to remove any translation and overall molecular rotation during the simulations.

Enzyme-Substrate Interactions

The energy for the enzyme-substrate interactions was calculated as a sum of electrostatic and van der Waals energy between atom pairs.

$$\Sigma_{pro-subs} = \Sigma(E_{el} + E_{vdw}) \quad \text{(Eq. 9)}$$

$E_{el}$ is the electrostatic contribution, $E_{vdw}$ is the van der Waals term and the summation runs over all atom pairs for the protein-substrate complex. The $E_{el}$ and $E_{vdw}$ terms were computed as follows, $$E_{el} = \frac{q_i q_j}{\varepsilon(r) r_{ij}} \text{ and } E_{vdw} = \frac{A_{ij}}{r_{ij}^{12}} - \frac{B_{ij}}{r_{ij}^{6}} \quad \text{(Eq. 10)}$$

where $q_i$ are partial charges, and $A_{ij}$, $B_{ij}$ are Lennard-Jones parameters. These parameters were obtained from the AMBER force field. A distance-dependent dielectric function was used:

$$\varepsilon(r_{ij}) = A + \frac{B}{1 + k\exp(-\lambda B r_{ij})} \quad \text{(Eq. 10)}$$

$B = \varepsilon_o - A$; $\varepsilon_o = 78.4$ for water; $A = -8.5525$; $\lambda = 0.003627$ and $k = 7.7839$.

All enzyme and substrate atom pairs were included in the calculations and resulting interaction energies were summed up per residue pair. The energies were calculated for 10,000 snapshots, every 20 ps, sampled during the full 200 ns simulation and were averaged over these 10,000 snapshots.

Loop Engineering Results

For $BChE_{G117H}$ two surface loops (residues 276-283 and 373-380) were identified by computational modeling that showed large, dynamical motions coupled with the hydrolysis of paraoxon in the active site. The octapeptide comprising residues 276-283 ($^{276}$FVVPYGTP$^{283}$) in particular showed enhanced catalysis-associated dynamics. This loop was selected as the initial target of engineering. It was hypothesized that increasing the length of this loop through insertions of residues with long hydrophilic side chains to increase the surface area for thermodynamical coupling would improve the rate of catalysis of $BChE_{G117H}$.

To address the concern regarding change of secondary structure of the surface loop with insertions of the residues as well as obtain ideas of suitable residues at these sites, a BLASTP search was performed which identified a subject annotated as serine carboxypeptidase with the matched sequence of $^{78}$FVVEPYNGTIP$^{88}$. Unfortunately, a structure of this protein was not available. A homology search with the identified serine carboxypeptidase, further identified wheat serine carboxypeptidase (PDB code 1BCR), whose structure indicates the corresponding region is on the surface as a partial loop.

Based on this additional information, it was postulated that inserting an additional three residues, a glutamate between V278 and P279, an asparagine between Y280 and G281, and a variable residue between T282 and P283 of $BChE_{G117H}$ would enhance dynamics and increase interaction with the solvent without significantly affecting the overall protein structure (FIG. 18). Instead of using a fixed residue I in the third position, VNK was incorporated in the primer to encode a wild card residue (A, D, E, G, H, I, K, L, M, N, P, Q, R, S, T, or V).

FIG. 18 shows the surface loop in BChE (residues 276-283) in the white circle. Thin blue lines indicate rigid areas while green to red areas with thicker tubes correspond to regions displaying large conformational fluctuations. Red residues are residues inserted into the loop sequence. In addition to E and N as the first two insertions, five different residues were considered at the third insertions site.

FIG. 19 shows results of computational modeling to characterize the effect of increasing the length of the engineered loop on dynamics. Starting from the $BChE_{G117H}$, one (E), two (E, N) and three (E, N, I) residues were inserted in the positions described above. Computational modeling based on MD simulations indicated that the dynamical flexibility increased markedly with insertion of three residues, while inserting only one led to a slight increase and inserting two showed a slight decrease. These results indicate that insertion of selected residues into the loop sequence may "fine tune" the structure enabling more interactions and increased loop dynamics, as predicted.

Inhibitor/Substrate Binding in the Active Site: Results

Simulations of enzyme-substrate interactions of $BChE_{G117H}$ and the five loop mutants indicated that OP substrates bound poorly to the active site region. Table 1 shows the interaction energies from conformational snapshots sampled during the MD simulations, and estimated using a sum of electrostatics and van der Waals interactions between the substrate and enzyme residues. In addition, the MD trajectories were also analyzed for enzyme-substrate interaction behavior.

TABLE 1

Enzyme-substrate interaction energy obtained from computations. Averaged interaction energies (in kcal/mol) between substrate and full enzyme (all residues) and only the catalytic triad (residues H117, S198, and H438).

|  | BCh (174.262[a]) | | paraoxon (275.195[a]) | | DFP (184.146[a]) | | echothiophate (383.228[a]) | |
| --- | --- | --- | --- | --- | --- | --- | --- | --- |
|  | enzyme | triad | enzyme | triad | enzyme | triad | enzyme | triad |
| G117H | −34.84 | −8.45 | −35.36 | −2.41 | −10.29 | −0.43 | −33.96 | −4.98 |
| ENI | −32.34 | −8.40 | −38.86 | −9.17[b] | −23.05 | −3.15 | −39.61 | −9.62[b] |
| ENG | −31.50 | −8.42 | −37.88 | −7.91[b] | −10.73 | −1.49 | −35.59 | −7.29[b] |
| ENA | −31.26 | −8.14 | −33.62 | −1.36 | −24.34 | −4.87 | −39.99 | −10.17[b] |
| ENT | −31.48 | −8.21 | −35.89 | −5.03 | −21.83 | −3.29 | −39.45 | −6.74[b] |
| ENR | −33.13 | −9.22 | −34.08 | −1.78 | −24.77 | −4.52 | −36.15 | −8.46[b] |

[a]molecular weight,
[b]indicates interaction ≥ in strength to native substrate.

Relatively similar interactions were noted between BCh as substrate and $BChE_{G117H}$ and the loop mutants, with the substrate remaining in the active site region for a relatively prolonged time (full 200 ns of MD trajectory). In contrast, when an OP substrate was modeled, it left the active site more rapidly (around 100 nanoseconds or less). These differences are reflected in Table 1, with lesser negative values in the case of the OPs.

With paraoxon, (except with the ENI mutant) the substrate completely avoided the active site pocket after 50 ns or less, making only minimal contacts with the protein surface. With the ENI mutant, paraoxon remained in the active site with its aromatic group maintaining its original conformation while other moieties sampled alternate conformations. With DFP, the OP quickly left the active site pocket as well. Moreover, DFP interactions with $BChE_{G117H}$ suggested the OP completely dissociated from the protein and moved into the bulk-solvent indicating very weak interactions. Finally, with echothiophate, more stable interactions were noted with ENI and ENG mutants, but the OP also rapidly left the active site in $BChE_{G117H}$ and the ENA loop-mutant. Interestingly, simulations with DFP suggested even lesser time-dependent interaction with the enzyme.

Note that in cases where the active site region showed poor binding, but the substrate still interacted with the protein, this was due to interactions with residues outside the active site. It should also be noted that OP substrates are larger than BCh and when interaction energy values are adjusted for molecular weight, the OP interaction with the enzymes appears even weaker.

Expression and Purification of BChE Loop Mutants

Six His-tagged monomeric mutants were constructed with three residue insertions into the residues 276-283 sequence with an identity of ENX, keeping glutamate and glutamine insertions constant but varying "X" with one of six different amino acids (A, G, I, P, R, and T). These mutants were produced by transfecting *Spodoptera frugiperda* Sf9 cells with a bacmid DNA-CellFECTIN mixture and purified using a Q Sepharose Fast Flow column followed by a $Ni^{2+}$-NTA agarose column. Protein concentrations were determined on a NanoDrop Spectrophotometer (Thermo Scientific ND1000).

Substrate Kinetics with BTCh

Enzyme activity with the choline substrate was evaluated using a modified Ellman method using butyrylthiocholine (BTCh) as the substrate. The final concentration of BTCh was varied between 10 μM and 1 mM and change in absorbance was monitored at 412 nm for 5 min at 37° C. using a Spectramax M2 microplate reader (Molecular Devices; Sunnyvale, Calif.). Enzyme activity was estimated based on the rate of appearance of the reaction product, 2-nitro-5-thiobenzoate ($\varepsilon = 14,150$ $M^{-1}$ $cm^{-1}$) and was uniformly corrected for non-enzymatic substrate hydrolysis using enzyme-free controls. $V_{max}$ and $K_M$ were determined using non-linear regression with the Michaelis-Menten equation. Turnover number, $k_{cat}$, was calculated using the relationship $V_{max} = k_{cat}[E]$, where $[E]$ represents the concentration of BChE active sites in the reaction.

BTCh Substrate Kinetics Results:

Table 2 shows the kinetic parameters ($k_{cat}$, $K_M$, and $k_{cat}/K_M$) determined from the hydrolysis of butyrylthiocholine by $BChE_{G117H}$ and $BChE_{G117H}$-derived loop mutants (n=3 for each enzyme preparation). The turnover rate with BTCh was significantly reduced (40-84%) in all enzymes with loop insertions compared to $BChE_{G117H}$ ($F_{5,156} = 5.25$, p=0.0002). A significant effect was also found in $K_M$ values ($F_{5,156} = 58.1$, p<0.0001). Post hoc analysis indicated that ENG and ENR mutants had a significantly higher $K_M$ in comparison to $BChE_{G117H}$. These parameters together as the ratio $k_{cat}/K_M$ suggest that the catalytic efficiency of the loop mutants was reduced compared to $BChE_{G117H}$. Note that the mutants were designed based on computational identification of increased dynamics of the loop region during modeling of paraoxon hydrolysis.

TABLE 2

Comparison of substrate kinetics parameters of $BChE_{G117H}$ and loop-mutants using butyrylthiocholine as the substrate and analysis using the Michaelis-Menten equation. Values are reported as mean ± SEM. An asterisk indicates a significant difference compared to $BChE_{G117H}$.

| | $k_{cat}$[a] ($min^{-1}$) | $K_M$ (mM) | $k_{cat}/K_M$ ($min^{-1}$ $M^{-1}$) |
|---|---|---|---|
| G117H | 13884 ± 374 | 1.21 ± 0.06 | $11.5 \times 10^6$ |
| +ENI | 2207 ± 76* | 1.7 ± 0.10 | $1.3 \times 10^6$ |
| +ENA | 4024 ± 204* | 1.68 ± 0.14 | $2.4 \times 10^6$ |
| +ENG | 8363 ± 1280* | 2.66 ± 0.60* | $3.1 \times 10^6$ |
| +ENR | 2568 ± 359* | 3.68 ± 0.71* | $0.7 \times 10^6$ |
| +ENT | 5976 ± 251* | 1.84 ± 0.13 | $3.2 \times 10^6$ |

Resistance to Inhibition Assay

Resistance of $BChE_{G117H}$ and the loop mutants to inhibition by the OPs was evaluated. Working enzyme solutions were prepared prior to assay (2 μg/ml in 100 mM potassium phosphate buffer, pH 7.0). Twenty ng of $BChE_{G117H}$ or one of the loop mutants was added to either vehicle or paraoxon (50 μM), diisopropylfluorophosphate (5 μM) or echothiophate (100 μM) and allowed to pre-incubate for 10 min in a 96-well plate containing buffer (100 mM potassium phosphate, pH 7.0) and DTNB (0.5 mM). Following pre-incubation, 20 µl of BTCh (1 mM final concentration) was added to begin the reaction and enzyme activity was assayed as described above and plotted as percent of the respective vehicle control over time.

Resistance to Inhibition Results

Figure 20:
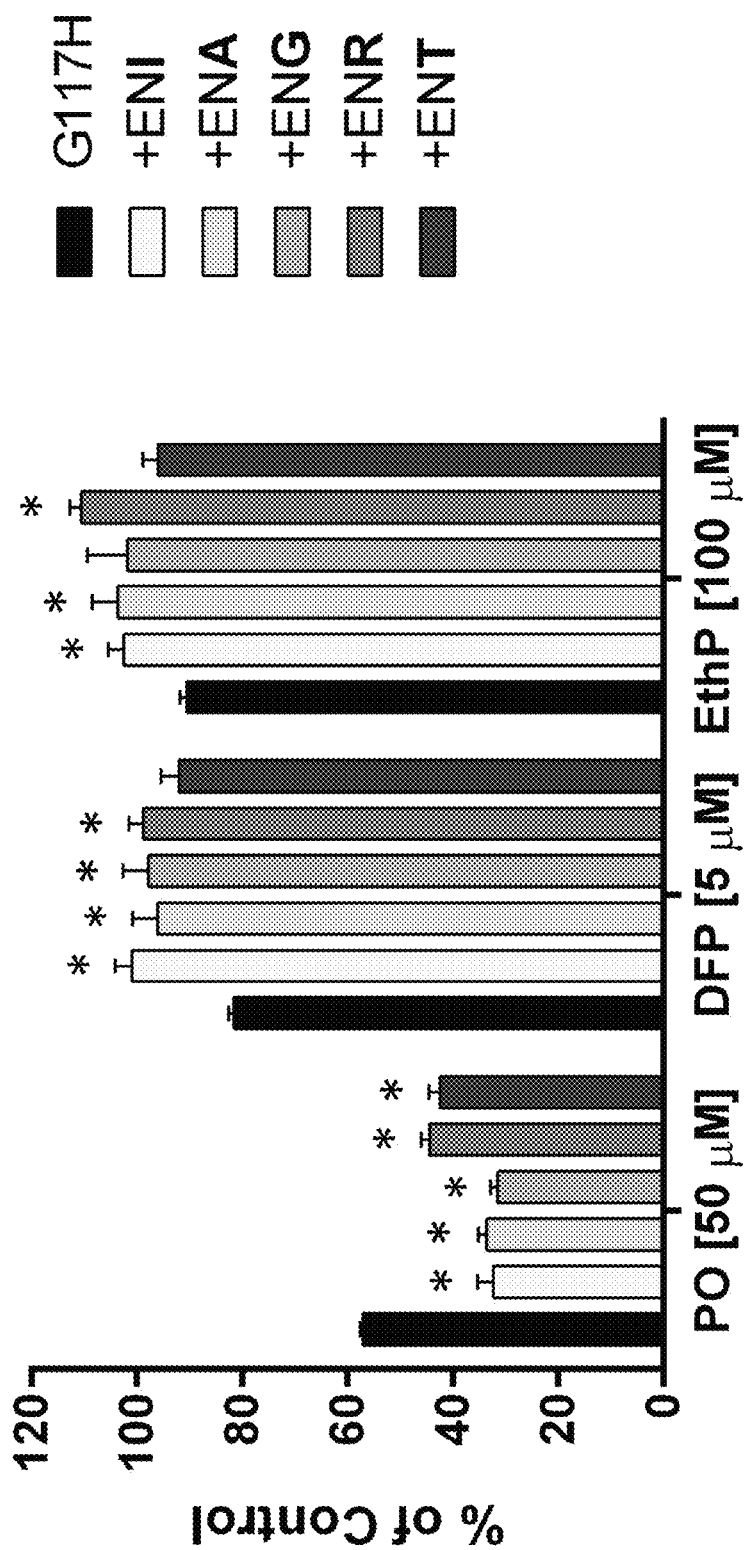
FIG. 20 depicts comparative resistance to inhibition of $BChE_{G117H}$ and loop mutants following a 10-min exposure to paraoxon (50 µM final), DFP (5 µM final) or EthP (100 µM final). Data represent the mean±standard error of the mean (SEM) of three independent replicates. An asterisk indicates a significant difference compared to $BChE_{G117H}$.

The enzyme's ability to resist inhibition by a high concentration of an OP following a 10-min incubation period was measured to evaluate enzyme-OP interactions, as shown in FIG. 20. Comparative resistance to inhibition of $BChE_{G117}$ and loop-mutants are shown as a percentage of control. Data represent the mean±SEM of three independent replicates. An asterisk indicates a significant difference compared to $BChEG_{117}$.

Preliminary assays allowed selection of OP concentrations that achieved near complete inhibition of $BChE_{G117}$ (>99%; data not shown). Under these conditions, using paraoxon, $BChE_{G117H}$ was somewhat more resistant to inhibition compared to all five loop-mutants studied, i.e., it retained 57% of its activity following paraoxon exposure while loop-mutants retained only 31-44% of pre-exposure activity). In contrast, when DFP was used as the inhibitor, the loop mutants were generally more resistant to inhibition. Specifically, ENI, ENA, ENG, and ENR mutants retained nearly full activity (96-100%) following DFP exposure, which was higher than noted with $BChE_{G117H}$ (82%). A similar finding was noted following exposure to EthP, with three loop mutants (ENI, ENA, and ENR) being more resistant to inhibition than $BChE_{G117H}$.

Figure 17:
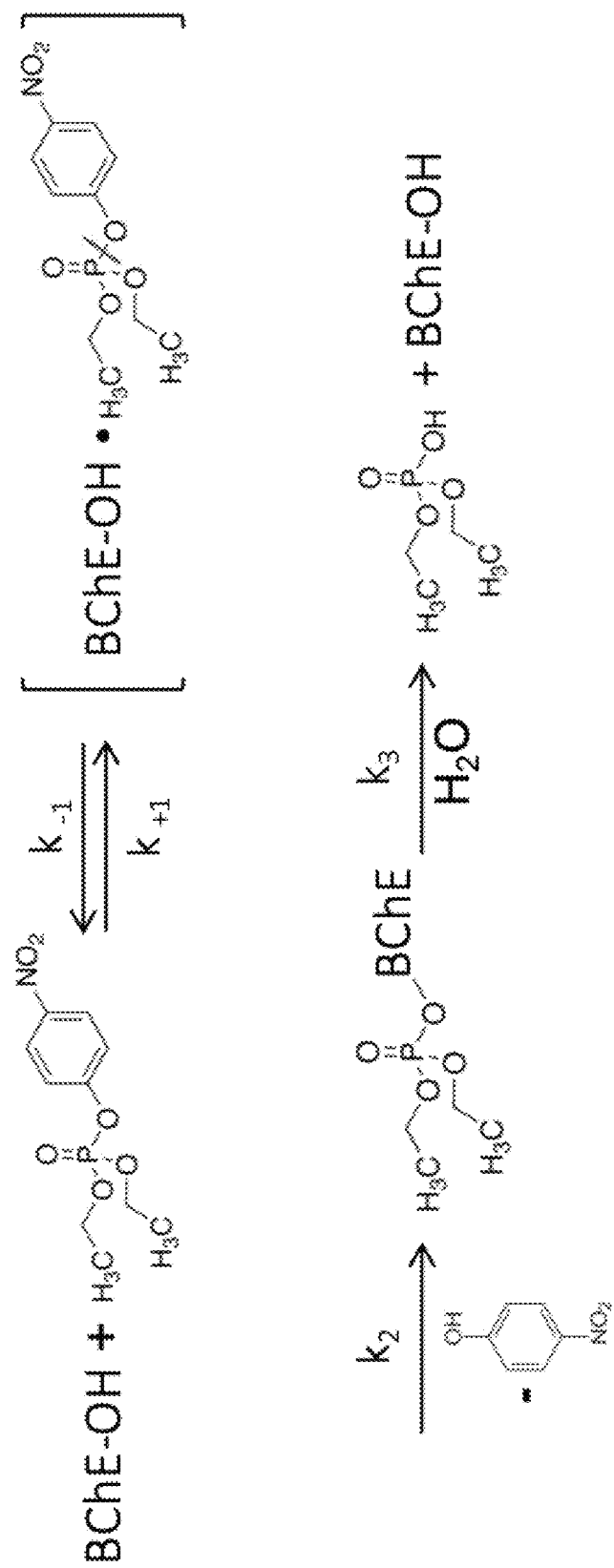
FIG. 17 depicts the schematic of mechanism of hydrolysis of a model OP toxicant (paraoxon) by BChE.
Figure 18:
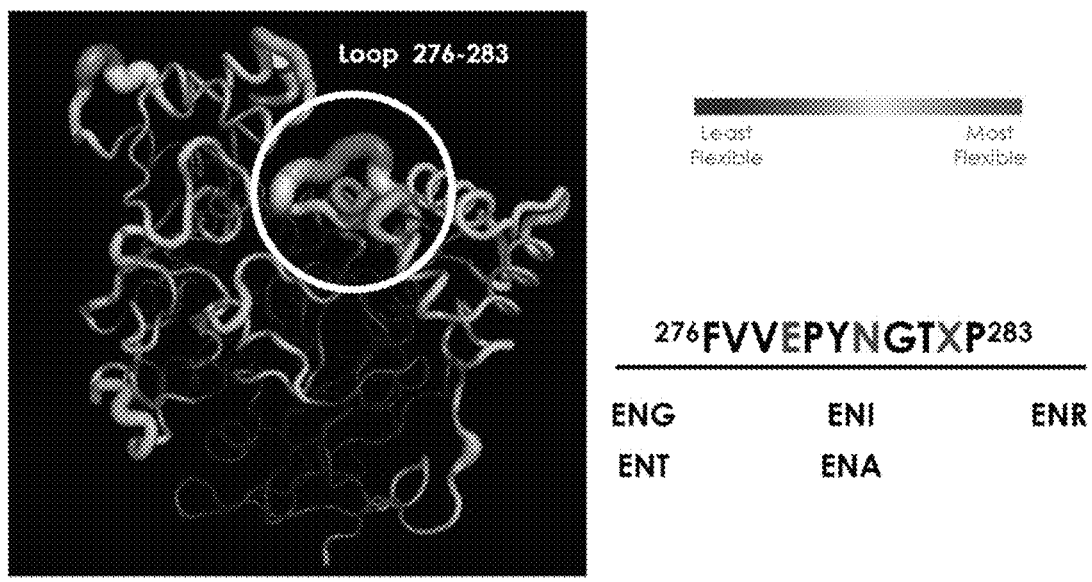
FIG. 18 depicts the surface loop of butyrylcholinesterase (residues 278-285) which was selected for protein engineering. The selected loop is in the highlighted circle. The protein sequence of the engineered loop is listed, with the residues inserted at the three positions highlighted. The 5 engineered loops (with inserts ENG, ENI, ENR, ENT and ENA) were designed.
Figure 19:
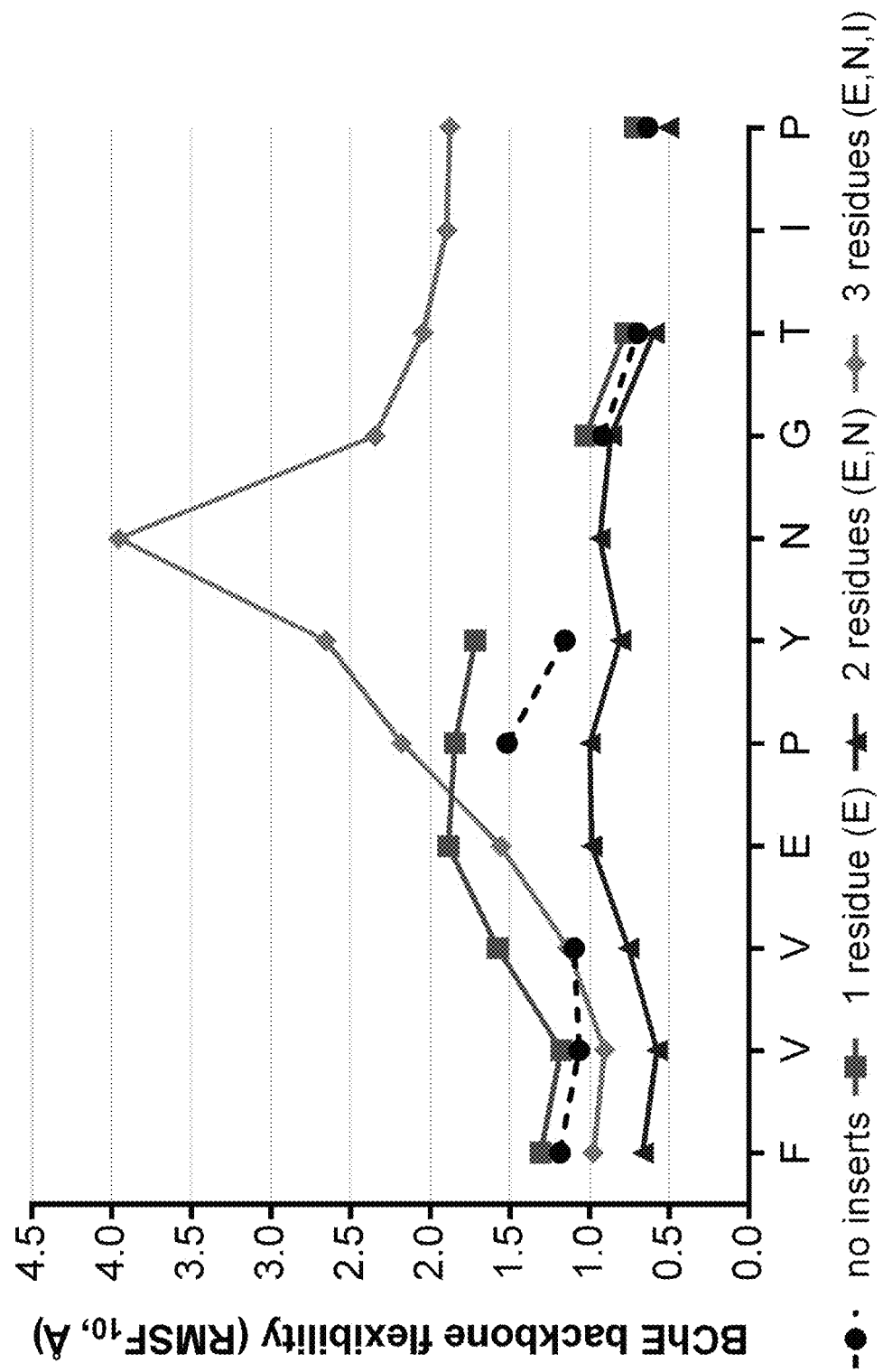
FIG. 19 is a line graph representing BChE backbone flexibility vs. number of protein residues inserted in the engineered loop as well as the location of the inserts.

Reactivation Rate ($k_3$) Determination:

Hydrolysis of OP compounds by BChE proceeds as shown in FIG. 17. First, an OP and BChE form a reversible Michaelis-complex ($k_1/k_{-1}$), however the bond quickly progresses through this step to phosphorylation at a rate of $k_2$. Spontaneous reactivation ($k_3$) does not occur at an appreciable rate in the wild-type enzyme, but is detectable in the mutant $BChE_{G117H}$.

The relative rate of dephosphylation ($k_3$), a measure of an enzyme's ability to reactivate after inhibition, can be used as an indicator of the catalytic rate. In brief, an equal volume of enzyme (20 µg/ml in 100 mM potassium phosphate buffer, pH 7.0) and OP (10 mM paraoxon or echothiophate) were pre-incubated for 1 min to achieve saturation of all enzyme active sites. Following incubation, a 5 µl sample was removed, rapidly diluted 400-fold into a cuvette containing the reaction components (0.5 mM DTNB and 1 mM BTCh in 100 mM potassium phosphate buffer, pH 7.0) and gently mixed. This large dilution reduces the final OP concentration to below its $K_M$, allowing dissociation of any OP molecules from the reversible Michaelis complexes.

Reactivation of the covalently bound enzyme was then followed at 412 nm at 37° C. as described above. As this assay is highly time-sensitive, the timing between sample transfer and initiation of absorbance readings was kept constant at 5 sec.

Reactivation Rate Results

This assay starts with putatively complete occupation of all active sites of the $BChE_{G117H}$ molecules by pre-incubation in an excess of an OP inhibitor. Following a marked (400-fold) dilution, any OP bound in a reversible Michaelis complex would dissociate, while OP molecules bound covalently to the active site serine would not. Thus, measuring the rate of recovery of catalytic activity under these conditions reflects the rate of dephosphylation. Baseline (100%) activity for each enzyme was estimated using enzyme without inhibitor.

Figure 21:
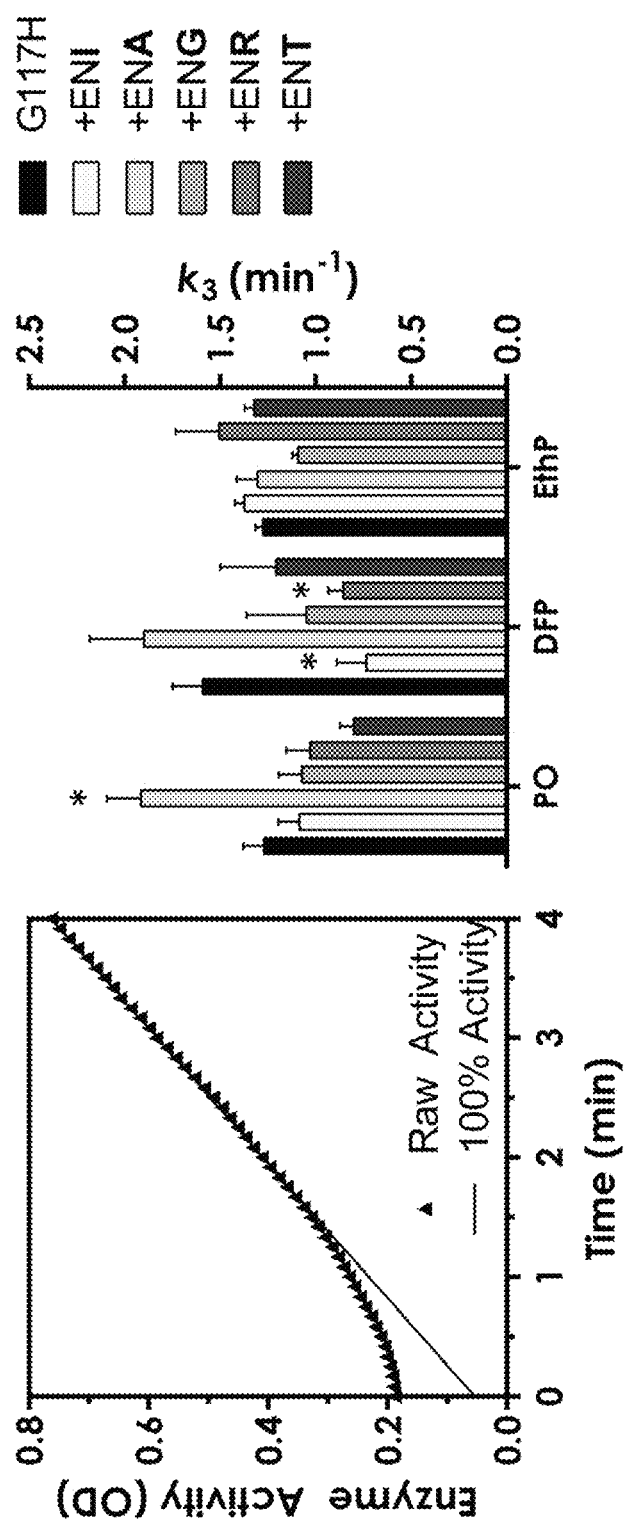
FIG. 21 depicts the recovery of activity in $BChE_{G117H}$ and loop mutants following exposure to 10 mM OP inhibitor (paraoxon, DFP or EthP). Left panel shows a representative plot of raw enzyme activity ($\Delta A_{412}$) following dilution including the reactivation and recovery phases. Right panel shows the mean±SEM of $k_3$ values.
Figure 22:
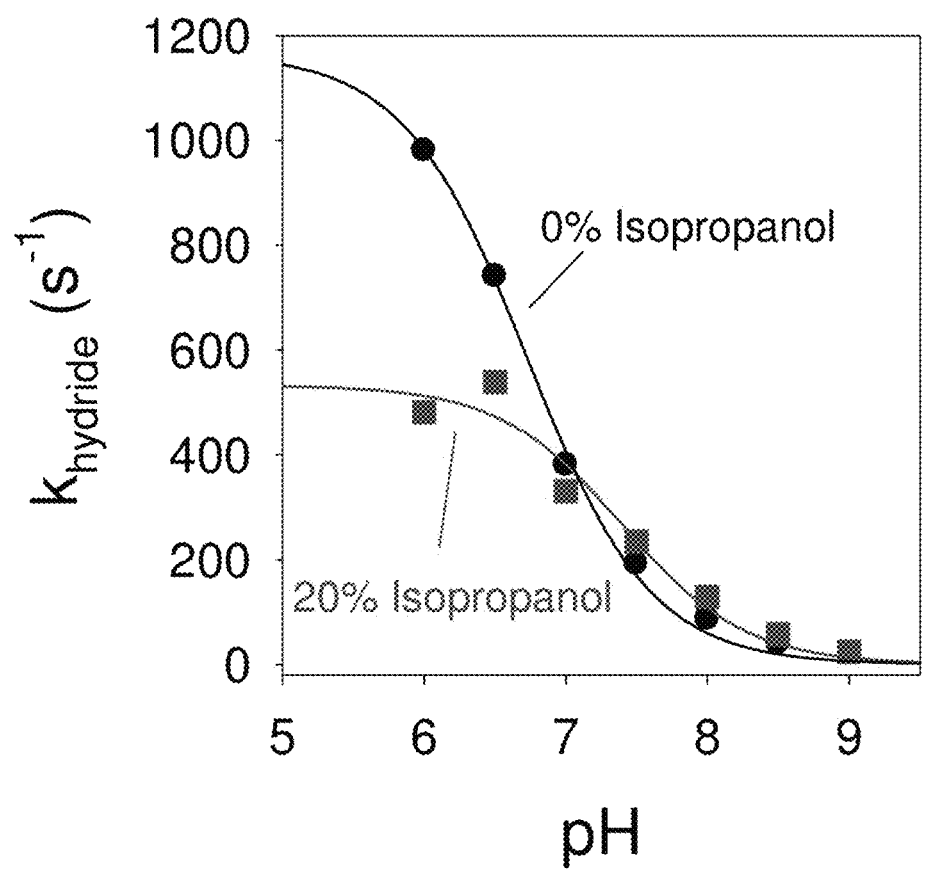
FIG. 22 illustrates the results of monitoring EcDHFR activity to determine the catalyzed hydride transfer rate using stopped-flow experiment. The rate is significantly decreased in presence of isopropanol.

FIG. 21 depicts a graph illustrating the recovery of activity in $BChE_{G117H}$ and loop mutants following exposure to 10 mM OP. Enzyme was allowed to react with the OP for one minute and then diluted 400-fold into a solution containing substrate (BTChI, 1 mM). The left graph shows a representative plot of raw enzyme activity ($\Delta A_{412}$) following dilution including the reactivation and recovery phases. The right graph shows the mean±SEM of $k_3$ values. In the case of DFP, 100% reactivation was not achieved, thus reported $k_3$ values have been corrected.

As shown in the left graph of FIG. 21, when paraoxon or echothiophate was used, all enzymes showed an initial reduction in activity followed by recovery to 100% of baseline. Interestingly, with DFP as the inhibitor, complete reactivation was not evident. The activity of $BChE_{G117H}$ returned to 67±2% of baseline while the various loop mutants showed recovery to 72-96% of baseline. The reactivation rate ($k_3$) was calculated by plotting the difference between observed and estimated values versus time during the recovery period. The $k_3$ values of $BChE_{G117H}$ with echothiophate (1.28 min$^{-1}$±0.04) and paraoxon (1.27 min$^{-1}$±0.11).

The ENA loop mutant showed a slight but significant increase in $k_3$ when pre-incubated with paraoxon, but no differences in $k_3$ were noted with the ENA mutant using DFP or echothiophate. In contrast, the right graph of FIG. 11 shows the $k_3$ of the ENI and ENR loop mutants with DFP was significantly decreased.

Paraoxon Hydrolysis

Hydrolysis of the OP substrate paraoxon was determined using a direct photometric assay. $BChE_{G117H}$ and the loop mutants were diluted to 0.06 mg/ml using PBS. A stock solution of paraoxon (in dry ethanol) was diluted on the day of assay and added to the reaction in final concentrations between 10-500 µM (with 5% ethanol included in all reactions). The final reaction volume of 100 µl contained 7.5 µl diluted enzyme and 72.5 µl 100 mM and 50 mM potassium phosphate buffer (pH 7.0), with the reaction being initiated by adding a 20 µl aliquot of paraoxon. The p-nitrophenol produced by hydrolysis of paraoxon was monitored at 405 nm for 1 h at 37° C. The extinction coefficient of p-nitrophenol ($\varepsilon$=18,500 M$^{-1}$ cm$^{-1}$) was used to determine enzyme activity, corrected by subtracting non-enzymatic hydrolysis. Kinetic parameters were determined using non-linear regression with the Michaelis-Menten equation.

Paraoxon Hydrolysis Results

Substrate kinetics with paraoxon suggested that all loop mutants had reduced catalytic activity compared to $BChE_{G117H}$. $K_M$ was significantly lower in the ENA mutant and there was a trend towards reduced $K_M$ with ENG and ENT (p=0.062 and p=0.052, respectively). Table 3 compares substrate kinetics among the different enzymes. The loop mutants ENA and ENG showed a trend towards higher catalytic efficiency ($k_{cat}/K_M$) compared to $BChE_{G117H}$, but this appeared driven by the changes in $K_M$ and not catalytic activity. Changes in substrate binding affinity could be critical in the kinetics of OP hydrolysis. Therefore, computational modeling was used to compare binding of paraoxon, echothiophate and DFP to $BChE_{G117H}$ and the selected engineered loop mutants.

TABLE 3

Figure 23:
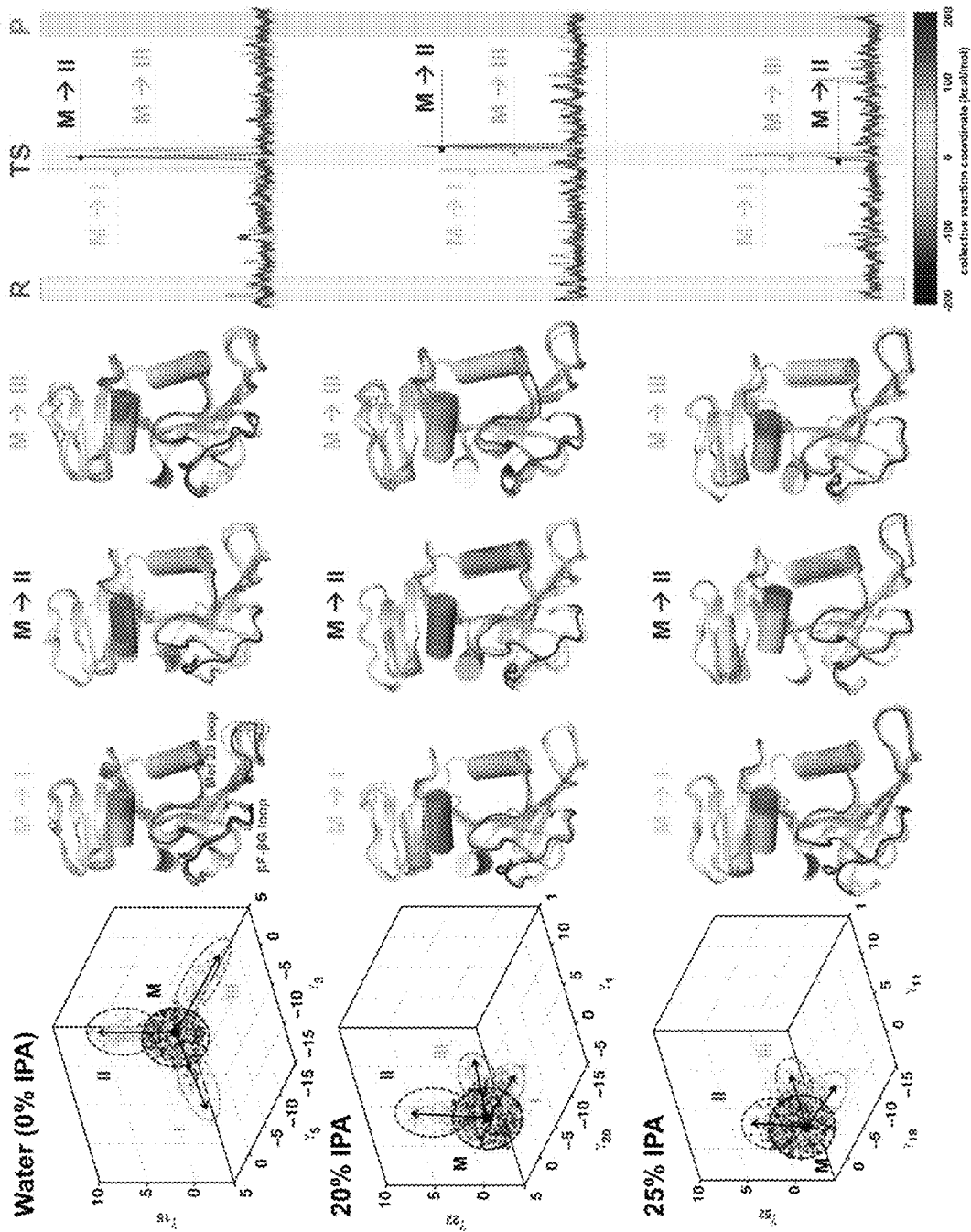
FIG. 23 illustrates the results of quasi-harmonic analysis associated with the EcDHFR catalyzed hydride transfer reaction in increasing isopropanol concentrations. The left panels show the conformational sub-states associated with the catalyzed reaction; the three middle panels show the conformational fluctuations in the enzyme structure associated with the conformational transitions into the TS sub-states. The right most panel shows the activation of the enzyme conformations near the TS during the catalyzed reaction.

Comparison of the substrate kinetics parameters of $BChE_{G117H}$ and loop mutants using paraoxon as the substrate. Kinetic analysis was determined using non-linear regression with the classic Michaelis-Menten equation. Values are reported as mean ± SEM. An asterisk indicates a significant difference compared to $BChE_{G117H}$.

| | $k_{cat}$ [a, b] ($min^{-1}$) | $K_M$ [b] (μM) | $k_{cat}/K_M$ [b] ($min^{-1}$ $M^{-1}$) |
|---|---|---|---|
| G117H | 0.244 ± 0.03 | 107.6 ± 28.1 | $2.2 \times 10^3$ |
| ENI | 0.071 ± 0.003* | 75.82 ± 9.3 | $0.9 \times 10^3$ |
| ENA | 0.078 ± 0.004* | 19.72 ± 5.3* | $3.9 \times 10^3$ |
| ENG | 0.089 ± 0.005* | 24.23 ± 6.0* | $3.6 \times 10^3$ |
| ENR | 0.092 ± 0.005* | 77.62 ± 12.2 | $1.2 \times 10^3$ |
| ENT | 0.076 ± 0.005* | 23.59 ± 6.1* | $3.2 \times 10^3$ |

[a] $k_{cat} = V_{max}$/[enzyme active site]

Statistical Analyses

Differences in substrate kinetics parameters with both BTCh and paraoxon were evaluated using one-way ANOVA. For the resistance to inhibition and reactivation rate ($k_3$) assays, statistical differences were determined using two-way ANOVA with enzyme and OP as main effect variables. In all cases, a post hoc Dunnett's multiple comparisons test was performed to determine differences among $BChE_{G117H}$ and the loop mutants. All statistical tests were conducted using GraphPad Prism software (La Jolla, CA), version 6.0.

Discussion

Interestingly, the engineered loop mutants studied all had a reduced catalytic efficiency ($k_{cat}/K_M$) with the choline substrate, BTCh. It was unexpected that any of the mutants would improve the catalytic rate using the choline substrate as it is already operating near the rate of diffusion (maximal speed). This is supported by the similar observation that $BChE_{G117H}$ also exhibits reduced activity with choline esters (e.g., butyrylthiocholine). The data also suggested that binding of the substrate with all the tested loop mutants was reduced relative to binding to $BChE_{G117H}$, suggesting the changes in the surface peptide network were indeed influencing physiochemical interactions in the active site region but in a negative manner relative to catalytic activity.

Two assays were conducted to evaluate the enzymes' interactions activities with three OPs. First, testing was performed to determine the enzymes' resistance to inhibition by a high concentration of OP. It should be noted that with this assay, the mechanism of resistance cannot be fully appreciated, but a change in resistance to inhibition may reflect a change in catalytic activity or substrate binding. With DFP and echothiophate, the loop mutants ENI, ENA, and ENR were more resistant to inhibition than $BChE_{G117H}$. Surprisingly, all loop mutants were less resistant to inhibition by paraoxon compared to $BChE_{G117H}$.

These conflicting results suggested that the selected peptide insertions differentially affected interaction with the different OPs. To evaluate further a mechanism of altered interactions between the enzyme and substrates, enzyme reactivation was measured, which is relatively unaffected by changes in substrate binding. Using paraoxon as the substrate, only the ENA mutant showed an improved catalytic efficiency. This increase, however, was not evident when paraoxon hydrolysis was evaluated separately, wherein a significant decrease was found in both $k_{cat}$ and $K_M$. Taken together, these results suggested that the decreased $K_M$ with paraoxon had more impact on the enzyme's apparent efficiency than any increase in reactivation. Reactivation data with DFP and EthP did not show significant increases in $k_3$, suggesting that the noted increase in loop mutant resistance to inhibition is likely a reflection of altered binding.

Computer simulations of $BChE_{G117H}$ and the engineered loop mutants with the choline ester substrate butyrylcholine and selected OP compounds provided insights into the observed experimental findings. BCh had strong interactions with all enzymes tested. However, the OP substrates showed mostly weak interactions, with the substrate showing unstable binding in most cases, rapidly leaving the active site pocket in less than 50 nanoseconds. This implied that the enzyme had limited time for effective hydrolysis. Interestingly the loop mutants showed slightly improved interactions with the OP substrates, particularly, paraoxon and echothiophate. This was supported by the increased $k_{cat}/K_M$ for these mutants over $BChE_{G117H}$.

In conclusion, surface loop insertions on $BChE_{G117H}$ resulted in changes in catalysis but appeared to decrease stability of the OP substrates within the active site region. Substrate/inhibitor-specific differences were noted between $BChE_{G117H}$ and the loop mutants with substrate kinetics and resistance to inhibition assays. There was a slight but significant increase in the dephosphylation rate constant with paraoxon with one (ENA) loop mutant.

The data suggest that increasing the interaction of identified hypermobile surface loops with the solvent yield improved catalytic interactions between OP-hydrolyzing enzymes and their substrates. Further emphasis on substrate stability within the active site of mutants may be important in future studies. While other OP hydrolases (e.g., paraoxonase, phosphotriesterase) have their own difficulties for prophylactic applications (e.g, immunogenicity, more limited substrate specificity), catalytic bioscavengers with higher intrinsic activity may be better candidates for evaluating the role of surface loop dynamics in enhancing OP hydrolysis.

Example 4: Controlling the Enzyme Activity by Solvent Conditions that Change Functionally Important Dynamics of Surface Loops The discovered connection between the enzyme surface residues/loop regions and solvent through the thermo-dynamical coupling can be used to modulate the enzyme activity. In particular, using the knowledge of network residues and location of the functionally important dynamical surface sites and their functional groups that interact with the solvent can be used to select solvent conditions to alter the energy coupling.

In one example, screening of solvents was performed with miscible organic solvents including methanol, ethanol, isopropanol, DMSO (dimethylsulfoxide), and acetonitrile to screen for aqueous mixture that changes the enzyme activity. Isopropanol provided the most interesting results. FIG. 22 shows the results of monitoring DHFR with stopped-flow kinetics to determine the hydride transfer rate. The pH independent rate for hydride transfer is 1170±10 $s^{-1}$ (black curve) for 0% isopropanol (buffer only), while it is 530±10 $s^{-1}$ with 20% isopropanol. Use of binary mixture of isopropanol and water indicated that the hydride transfer by *E. coli* DHFR under rate limiting conditions (measure by steady state kinetics) shows 2.2-fold decrease, at 20% isopropanol concentration.

X-ray crystallography showed no change in enzyme structure, however, quasi-elastic neutron scattering shows that enzyme motions are suppressed with increasing concentration of isopropanol. Computational modeling indicated that there is no change in active site structural or electrostatic environment but the access to conformational sub-states is altered significantly. In particular, the rate of transitions into functionally relevant conformational sub-states was about 3-fold smaller, close to the experimentally observed decrease in hydride transfer rate as depicted in FIG. 23.

Collectively, using experimental techniques (including steady state enzyme kinetics, X-ray crystallography, neutron scattering and isothermal calorimetry) and computational methods indicates that solvent conditions altered the energetic landscape such that enzyme is unable to sample the natural motions required for accessing the functionally relevant conformational sub-states. These results have important implication for investigating enzyme mechanisms in vivo as the cellular conditions could impact dynamics and therefore catalysis.

In general, this approach can be used to design solvent conditions that either enhance or decrease the enzyme activity based on increasing and decreasing thermo-dynamical coupling between the surface regions (in functionally important areas) and solvent. Such changes in the thermo-dynamical coupling will also reflect in the changes in the conformational sub-states populations related to the functional states, such as the transition state.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method of engineering a target enzyme to modify its catalytic activity, the method comprising:
   accessing biophysical and dynamics data for the target enzyme;
   analyzing, using a computing device, the biophysical and dynamics data to identify at least one energy transfer network within the target enzyme, the at least one energy transfer network comprising a series of residues spanning from a surface of the target enzyme to a catalytic site of the target enzyme;
   identifying at least one surface loop or neighboring region within the at least one energy transfer network, wherein the at least one surface loop or neighboring region comprises one or more residues showing promoting dynamical motions coupled to the catalytic activity of the target enzyme;
   iteratively modifying at least one residue of the one or more residues of the at least one surface loop or neighboring region to produce a plurality of candidate engineered enzyme sequences such that each of the plurality of candidate engineered enzyme sequences comprises a different residue at the location of the at least one residue, wherein the at least one surface loop or neighboring region has a longer side chain as a result of the modifying;
   for each candidate engineered enzyme sequence of the plurality of candidate engineered enzyme sequences:
      determining a modified network conductance of the candidate engineered enzyme sequence exceeds a baseline network conductance of the target enzyme and provides an increase in energy flow directed into the catalytic site via the at least one energy transfer network by:
         calculating a residue energy conductance for each residue of the at least one energy transfer network for each of the target enzyme and the candidate engineered enzyme sequence; and
         combining the residue energy conductance for each residue of the at least one energy transfer network for each of the baseline network conductance and the modified network conductance;
   calculating the change in thermo-dynamical coupling with an external environment or solvent by calculating the surface area of interaction due to the modified residue;
   calculating the changes in conformations in the functionally important sub-states related to the enzyme activity due to the changes in energy conductance through the network;
   assigning a score or ranking of each candidate engineered enzyme sequence of the plurality of candidate engineered enzyme sequences using the modified network conductance, the change in thermo-dynamical coupling, and the changes in conformations;
   selecting a subset of top ranking candidates of the plurality of candidate engineered enzyme sequences; and
   constructing an engineered enzyme with increased catalytic activity by transfecting cells with nucleic acids encoding the engineered enzyme sequence selected from the subset of top ranking candidates and purifying the engineered enzyme.

2. The method of claim 1, wherein the biophysical and dynamics data is obtained by computational analysis of internal movements of the target enzyme that affect its catalytic activity.

3. The method of claim 1, wherein the biophysical and dynamics data is obtained by one or more approaches including root-mean-square-fluctuations (RMSF) analysis, time-averaged normal coordinate analysis (TANCA), quasi-harmonic analysis (QHA), and quasi-anharmonic analysis (QAA).

4. The method of claim 1, further comprising modeling the engineered enzyme in complex with a substrate using molecular modeling simulations.

5. The method of claim 1, wherein the at least one surface loop comprises at least two residues.

6. The method of claim 1, wherein modifying the at least one surface loop or neighboring region comprises inserting at least one additional residue.

7. The method of claim 1, further comprising outputting an amino acid sequence for the engineered enzyme.

8. The method of claim 1, further comprising analyzing kinetics of catalytic conversion of a substrate to product by the engineered enzyme, using one or more of methods including spectrophotometric assays, radiometric assays, mass spectrometry, multiple injection method studies, isothermal titration calorimetry studies, stopped-flow kinetics, steady state kinetics, and pre-steady state kinetics measurements.

9. The method of claim 1, wherein modifying one or more residues of the at least one surface loop or neighboring region comprises modifying a sequence of the one or more residues of the at least one surface loop or neighboring region.

10. The method of claim 1, wherein modifying the at least one residue of the one or more residues of the at least one surface loop or neighboring region comprises improving the strength of hydrogen bonding or hydrophobic interaction with the network residue, located away from the surface.

11. The method of claim 1, wherein each residue energy conductance is calculated using coordinate and velocity data obtained using molecular dynamics simulations.

12. The method of claim 1, wherein calculating the residue energy conductance comprises a sum of all heat fluxes entering and existing the each residue.

13. The method of claim 1, wherein combining the residue energy conductance comprises taking an average of the residue energy conductance of the at least one energy network.

14. The method of claim 1, wherein combining the residue energy conductance comprises multiplying the residue energy conductance of the at least one energy network.

15. The method of claim 1, wherein the surface area of interaction between the residue and environment or solvent is calculated based on the coordinate data obtained using molecular modeling simulations.

16. The method of claim 1, wherein the populations in functionally important conformational sub-states related to the enzyme activity is obtained using molecular modeling simulations.

17. The method of claim 16, wherein the populations information is obtained using one or more of root-mean-square-fluctuations (RMSF) analysis, time-averaged normal coordinate analysis (TANCA), quasi-harmonic analysis (QHA), and quasi-anharmonic analysis (QAA).

18. The method of claim 1, wherein the biophysical and dynamics data is obtained by one or more of nuclear magnetic resonance (NMR), X-ray crystallography, cryogenic electron microscopy (Cryo-EM), neutron scattering, and hydrogen deuterium exchange.

19. The method of claim 1, wherein the subset of top ranking candidates comprises a single top ranking candidate.

20. A method of engineering a target enzyme to modify its catalytic activity, the method comprising:
   accessing biophysical and dynamics data for the target enzyme;
   analyzing, using a computing device, the biophysical and dynamics data to identify at least one energy transfer network within the target enzyme, the at least one energy transfer network comprising a series of residues spanning from a surface of the target enzyme to a catalytic site of the target enzyme;
   identifying one or more residues within the energy transfer network that are not on the surface of the target enzyme;
   iteratively modifying at least one of the one or more residues of the energy transfer network to produce a plurality of candidate engineered enzyme sequences such that each of the plurality of candidate engineered enzyme sequences comprises a different residue at the location of the at least one residue, wherein at least one surface loop or neighboring region has longer side chains as a result of the modifying;
   for each candidate engineered enzyme sequence of the plurality of candidate engineered enzyme sequences:
      determining a modified network conductance of the engineered enzyme sequence exceeds a baseline network conductance of the target enzyme and provides an increase in energy flow to the catalytic site, via the at least one energy transfer network by:
         calculating a residue energy conductance for each residue of the at least one energy transfer network for each of the target enzyme and the engineered enzyme sequence; and
         combining the residue energy conductance for each residue of the at least one energy transfer network for each of the baseline network conductance and the modified network conductance;
      calculating the change in thermo-dynamical coupling with an external environment or solvent by calculating the surface area of interaction due to the modified residue;
      calculating the changes in conformations in functionally important sub-states related to the enzyme activity due to the changes in energy conductance through the network;
      assigning a score or ranking of each candidate engineered enzyme sequence of the plurality of candidate engineered enzyme sequences using the modified network conductance, the change in thermo-dynamical coupling, and the changes in conformations;
   selecting a subset of top ranking candidates of the plurality of candidate engineered enzyme sequences; and
   constructing an engineered enzyme with increased catalytic activity by transfecting cells with nucleic acids encoding the engineered enzyme sequence selected from the subset of top ranking candidates and purifying the engineered enzyme.

21. The method of claim 20, where the improved energy flow is determined by performing molecular modeling simulations with a temperature gradient and measuring improved energy conductance in the one or more residues as modified.

22. The method of claim 20, further comprising measuring the catalytic activity of substrate conversion to product by the engineered enzyme by one or more of spectrophotometric assays, radiometric assays, mass spectrometry, multiple injection method studies, isothermal titration calorimetry studies, stopped-flow kinetics, steady state kinetics, and pre-steady state kinetics measurements.

23. The method of claim 20, wherein the biophysical and dynamics data is obtained by one or more of nuclear magnetic resonance (NMR), X-ray crystallography, cryogenic electron microscopy (Cryo-EM), neutron scattering, and hydrogen deuterium exchange.

24. A method of immobilizing an enzyme to preserve naturally occurring activity, the method comprising:
   accessing biophysical and dynamics data for the target enzyme;
   analyzing, using a computing device, the biophysical and dynamics data to identify at least one energy transfer network within the target enzyme, the at least one energy transfer network comprising a series of residues spanning from a surface of the target enzyme to a catalytic site of the target enzyme;
   identifying one or more residues that are not within the energy transfer network and are not on the surface of the target enzyme, wherein the one or more residues show higher energy conductance than an average values of all the enzyme residues, wherein each residue energy conductance is determined by:
      calculating a residue energy conductance for each residue of the at least one energy transfer network for each of the target enzyme and the engineered enzyme sequence; and
      combining the residue energy conductance for each residue of the at least one energy transfer network for each of the baseline network conductance and the modified network conductance;
   calculating the change in thermo-dynamical coupling with an external environment or solvent by calculating the surface area of interaction due to the modified residue; and
   immobilizing the target enzyme using the one or more residues identified as not part of the energy network.

25. The method of claim 24, wherein the biophysical and dynamics data is obtained by one or more of nuclear magnetic resonance (NMR), X-ray crystallography, cryogenic electron microscopy (Cryo-EM), neutron scattering, and hydrogen deuterium exchange.

26. A method of engineering a target enzyme to modify its catalytic activity, the method comprising:
- accessing biophysical and dynamics data for the target enzyme;
- analyzing, using a computing device, the biophysical and dynamics data to identify at least one energy transfer network within the target enzyme, the at least one energy transfer network comprising a series of residues spanning from a surface of the target enzyme to a catalytic site of the target enzyme;
- identifying at least one surface loop within the energy transfer network, the at least one surface loop or neighboring region comprising one or more residues showing demoting dynamical motions coupled to the catalytic activity of the target enzyme;
- iteratively modifying one or more residues out of the at least one surface loop or neighboring region to produce a plurality of candidate engineered enzyme sequences such that each of the plurality of candidate engineered enzyme comprises a different residue at the location of the at least one residue, wherein the at least one surface loop or neighboring region has shorter side chains as a result of the modifying;
- for each candidate engineered enzyme sequence of the plurality of candidate engineered enzyme sequences:
    - determining a modified network conductance of the engineered enzyme sequence exceeds a baseline network conductance of the target enzyme and provides a decrease in energy flow with decreased dynamics and decreased energy transfer directed into the active site via the at least one energy transfer network by:
        - calculating a residue energy conductance for each residue of the at least one energy transfer network for each of the target enzyme and the engineered enzyme sequence; and
        - combining the residue energy conductance for each residue of the at least one energy transfer network for each of the baseline network conductance and the modified network conductance;
- calculating the change in thermo-dynamical coupling with an external environment or solvent by calculating the surface area of interaction due to the modified residue;
- calculating the changes in conformations in the functionally important sub-states related to the enzyme activity due to the changes in energy conductance through the network;
- assigning a score or ranking of each candidate engineered enzyme sequence of the plurality of candidate engineered enzyme sequences using the modified network conductance, the change in thermo-dynamical coupling, and the changes in conformations;
- selecting a subset of top ranking candidates of the plurality of candidate engineered enzyme sequences; and
- constructing an engineered enzyme with decreased catalytic activity by transfecting cells with nucleic acids encoding the engineered enzyme sequence selected from the subset of top ranking candidates and purifying the engineered enzyme.

27. The method of claim 26, further comprising deleting at least one or more of residues of the at least one surface loop or neighboring region, to decrease the energy transfer along the network by measuring energy conductance with at least 1% decrease.

* * * * *